US008535886B2

(12) United States Patent
Patel et al.

(10) Patent No.: US 8,535,886 B2
(45) Date of Patent: Sep. 17, 2013

(54) METHODS AND COMPOSITIONS FOR NUCLEIC ACID SAMPLE PREPARATION

(75) Inventors: Pranav Patel, Fremont, CA (US); Keith Bjornson, Newark, CA (US); Kevin Travers, Santa Clara, CA (US); Cheryl Heiner, San Mateo, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 13/494,729

(22) Filed: Jun. 12, 2012

(65) Prior Publication Data

US 2012/0309650 A1 Dec. 6, 2012

Related U.S. Application Data

(63) Continuation of application No. 12/383,855, filed on Mar. 27, 2009, now Pat. No. 8,236,499.

(60) Provisional application No. 61/072,160, filed on Mar. 28, 2008.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl.
USPC ......... 435/6.1; 435/6.11; 435/6.12; 435/91.1; 435/91.2; 536/23.1; 536/24.3; 536/24.33; 536/25.3

(58) Field of Classification Search
USPC ........ 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| | | |
|---|---|---|
| 5,001,050 A | 3/1991 | Blanco et al. |
| 5,162,654 A | 11/1992 | Kostichka et al. |
| 5,198,543 A | 3/1993 | Blanco et al. |
| 5,350,686 A | 9/1994 | Jhingah |
| 5,470,724 A | 11/1995 | Ahern |
| 5,547,839 A | 8/1996 | Dower et al. |
| 5,576,204 A | 11/1996 | Blanco et al. |
| 5,629,468 A | 5/1997 | Schwarz et al. |
| 5,648,245 A | 7/1997 | Fire et al. |
| 5,674,683 A | 10/1997 | Kool |
| 5,674,716 A | 10/1997 | Tabor et al. |
| 5,714,320 A | 2/1998 | Kool |
| 5,854,033 A | 12/1998 | Lizardi |
| 5,948,616 A | 9/1999 | Chao et al. |
| 6,080,545 A | 6/2000 | Popoff et al. |
| 6,087,099 A | 7/2000 | Gupte et al. |
| 6,103,465 A | 8/2000 | Johnston-Dow et al. |
| 6,143,495 A | 11/2000 | Lizardi et al. |
| 6,210,891 B1 | 4/2001 | Nyren et al. |
| 6,210,896 B1 | 4/2001 | Chan |
| 6,235,502 B1 | 5/2001 | Weissman et al. |
| 6,235,503 B1 | 5/2001 | Lindemann et al. |
| 6,251,610 B1 | 6/2001 | Gupte et al. |
| 6,255,083 B1 | 7/2001 | Williams |
| 6,261,808 B1 | 7/2001 | Auerbach |
| 6,287,824 B1 * | 9/2001 | Lizardi ......................... 435/91.2 |
| 6,291,187 B1 | 9/2001 | Kingsmore et al. |
| 6,369,038 B1 | 4/2002 | Blumenfeld et al. |
| 6,451,563 B1 | 9/2002 | Wittig et al. |
| 6,498,023 B1 | 12/2002 | Abarzua |
| 6,787,308 B2 | 9/2004 | Balasubramanian |
| 6,849,404 B2 | 2/2005 | Park et al. |
| 6,917,726 B2 | 7/2005 | Levene et al. |
| 7,013,054 B2 | 3/2006 | Levene et al. |
| 7,033,764 B2 | 4/2006 | Korlach et al. |
| 7,045,362 B2 | 5/2006 | Hartwich et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Korlach et al. |
| 7,181,122 B1 | 2/2007 | Levene et al. |
| 7,229,799 B2 | 6/2007 | Williams et al. |
| 7,282,337 B1 | 10/2007 | Harris et al. |
| 7,292,742 B2 | 11/2007 | Levene et al. |
| 7,361,466 B2 | 4/2008 | Korlach et al. |
| 7,368,265 B2 | 5/2008 | Brenner et al. |
| 7,416,844 B2 | 8/2008 | Korlach et al. |
| 7,476,503 B2 | 1/2009 | Turner et al. |
| 7,485,424 B2 | 2/2009 | Korlach et al. |
| 7,601,495 B2 | 10/2009 | Chen et al. |

(Continued)

FOREIGN PATENT DOCUMENTS

| | | |
|---|---|---|
| EP | 1225234 B1 | 11/2007 |
| EP | 1907573 B1 | 1/2010 |

(Continued)

OTHER PUBLICATIONS

Figures 1A and 1B of US 2007/0087358A1 with the examiner's handwritings. Printed on Oct. 5, 2012.
Bashir, A. et al., "Evaluation of paired-end sequencing strategies for detection of genome rearrangements in cancer" Plos CompBiol (2008) 4(4):1-14.
Eid, et al., "Real-time DNA sequencing from single polymerase molecules" Science (2009) 323(5910):133-138.
Harris, T.D. et al., "Single-molecule DNA sequencing of a viral genome" Science (2008) 320:106-109.
Hong, Y.S. et al., "Construction of a BAC library and generation of BAC end sequence-tagged connectors for genome sequencing" Mol Genet Genomics (2003) 268:720-728.
Koonin et al. "Computer-assisted dissection of rolling circle DNA replication" Biosystems (1993) 30(1-3):241-268.
Korbel, J.O. et al. "Paired-end mapping reveals extensive structural variation in the human genome" Science (2007) 318:420-426.

(Continued)

*Primary Examiner* — Frank Lu
(74) *Attorney, Agent, or Firm* — Deana A. Arnold

(57) ABSTRACT

Provided are methods and compositions for the production of linear single-stranded nucleic acids, which can be used as templates in high-throughput sequencing systems. Also provided are methods and compositions for the production of closed single-stranded nucleic acid loops, which can be used as templates in high-throughput sequencing systems.

15 Claims, 8 Drawing Sheets

(56) References Cited

U.S. PATENT DOCUMENTS

| | | | |
|---|---|---|---|
| 7,601,499 B2 | 10/2009 | Berka et al. | |
| 7,700,287 B2 | 4/2010 | Chen et al. | |
| 7,754,429 B2 | 7/2010 | Rigatti et al. | |
| 7,767,400 B2 | 8/2010 | Harris et al. | |
| 7,901,889 B2 | 3/2011 | Christians et al. | |
| 8,153,375 B2 | 4/2012 | Travers et al. | |
| 2001/0030290 A1 | 10/2001 | Stern | |
| 2003/0044781 A1 | 3/2003 | Korlach et al. | |
| 2003/0096253 A1 | 5/2003 | Nelson et al. | |
| 2003/0143550 A1 | 7/2003 | Green et al. | |
| 2003/0175729 A1 | 9/2003 | Van Eijk et al. | |
| 2003/0190647 A1 | 10/2003 | Odera | |
| 2003/0207279 A1 | 11/2003 | Crothers et al. | |
| 2003/0213771 A1 | 11/2003 | Ohshita et al. | |
| 2003/0215862 A1 | 11/2003 | Parce et al. | |
| 2004/0048300 A1 | 3/2004 | Sood et al. | |
| 2004/0152119 A1 | 8/2004 | Sood et al. | |
| 2004/0203008 A1 | 10/2004 | Uemori et al. | |
| 2004/0224319 A1 | 11/2004 | Sood et al. | |
| 2004/0259082 A1 | 12/2004 | Williams | |
| 2005/0176035 A1 | 8/2005 | Crothers et al. | |
| 2006/0061754 A1 | 3/2006 | Turner et al. | |
| 2006/0063171 A1 | 3/2006 | Akeson et al. | |
| 2006/0063264 A1 | 3/2006 | Turner et al. | |
| 2006/0292611 A1 | 12/2006 | Berka et al. | |
| 2007/0062934 A1 | 3/2007 | King | |
| 2007/0087358 A1 | 4/2007 | Ehrlich et al. | |
| 2007/0161017 A1 | 7/2007 | Eid et al. | |
| 2007/0178482 A1 | 8/2007 | Lezhava et al. | |
| 2007/0269825 A1 | 11/2007 | Wang et al. | |
| 2008/0026393 A1 | 1/2008 | Mindrinos et al. | |
| 2008/0233575 A1 | 9/2008 | Harris et al. | |
| 2009/0005252 A1 | 1/2009 | Drmanac et al. | |
| 2009/0181861 A1* | 7/2009 | Li et al. | 506/16 |
| 2009/0197257 A1 | 8/2009 | Harris | |
| 2009/0269771 A1 | 10/2009 | Schroeder | |
| 2009/0305248 A1 | 12/2009 | Lander et al. | |
| 2010/0121582 A1 | 5/2010 | Pan et al. | |
| 2011/0212436 A1 | 9/2011 | Christians et al. | |

FOREIGN PATENT DOCUMENTS

| | | |
|---|---|---|
| WO | 9106678 A1 | 5/1991 |
| WO | 9416090 A1 | 7/1994 |
| WO | 9627025 A1 | 9/1996 |
| WO | 9905315 A2 | 2/1999 |
| WO | 2007003017 A1 | 1/2007 |
| WO | 2007010263 A2 | 1/2007 |
| WO | 2007070572 | 6/2007 |
| WO | 2008058282 | 5/2008 |
| WO | 2009124255 A2 | 10/2009 |

OTHER PUBLICATIONS

Kuhn et al., "Rolling-circle amplificaiton under iopological constraints" Nucl Acids Res (2002) 30(2):574-580.

Levene et al., "Zero-mode waveguides for single-molecule analysis at high concentrations" Science (2003) 299 (5607):682-686.

Matray, T.J. et al. "A specific partner for abasic damage in DNA" Nature (1999) 399:704-708.

Myers, G. "Whole-genome DNA sequencing" IEEE (May-Jun. 1999) pp. 33-43.

Novick "Contrasting lifestyles of rolling-circle phages and plasmids" Trends Biochem Sci (1998) 23(11):434-438.

Reifenberger, J. et al., Advances in Genome Biol and Tech (AGBT) (2009) Abstract Feb. 4-7, 2009.

Reifenberger, J. et al., Biophys Soc 53rd Ann Meeting (2009) Abstract, Feb. 28, 2009.

Smith, M. et al., "Genomic sequence sampling: a strategy for high resolution sequence-based physical mapping of complex genomes" Nature Genetics (1994) 7:40-47.

Spinella et al.. "Tandem arrayed ligation of expressed sequence tags (TALEST): a new method for generating global gene expression profiles" Nucl Acids Res (1999) 27(18):e22-e22.

Velculescu et al. "Serial analysis of gene expression" Science (1995) 270(5235): 484-487.

Volik, S. et al., "End-sequence profiling: sequence-based analysis of aberrant genomes" PNAS (2003) 100 (13):7696-7701.

Wiley, G. et al., "Methods for generating shotgun and mixed shotgun/paired-end libraries for the 454 DNA sequencer" Current Protocols in Human Genomics (2009) Chapter 18; Unit 18,1, pp. 1-21.

Technology Spotlight: Illumina Sequencing Technology, current of Oct. 8, 2008, pp. 1-4.

Hormozdiari, et al., "Combinatorial algorithms for structural variation detection in high-throughput sequenced genomes," Genome Research (2009) 19:1270-1278.

Lee, et al. "A robust framework for detecting structural variations in a genome," Bioinformatics (2008) 24:i59-i67.

Margulies, et al., "Genome sequencing in microfabricated high-density picolitre reactors," Nature (2005), 437;376-382.

Pedler, "Occupation Times for Two State Markov Chains," Journ Appl Probability (1971), 8(2):381-90.

Svoboda, et al., "Fluctuation analysis of motor protein movement and single enzyme kinetics," PNAS (1994), 91:11782-86.

International Search Report and Written Opinion dated Oct. 27, 2009 for related case PCT/US2009/001930.

International Preliminary Report on Patentability dated Oct. 7, 2010 for related case PCT/US2009/001930.

International Search Report and Written Opinion dated Nov. 17, 2009 for related case PCT/US2009/001926.

Padegimas, L.S., "Adaptor Ligation-Based Polymerase Chain Reaction-Mediated Walking," Anal Biochem (1998) 260:149-153.

Metzker, M.I., "Emerging Technologies in DNA Sequencing," Genome Research (2005) 15:1767-1776.

Supplementary European Search Report dated Mar. 20, 2012 for related case EP09724672.2.

Ahn et al., "Inhibitory Effects of Novel AP-1 Decoy Oligodeoxynucleotides on Vascular Smooth Muscle Cell Proliferation In Vitro and Neointimal Formation In Vivo," Circulation Research (2002) 90:1325-1332.

The definition of "consensus sequence". Printed on Aug. 24, 2011.

First Office Action dated Nov. 20, 2012 for related case CN 200980115750.0.

First Office Action dated Jun. 5, 2013 for related case EP 09724672.2.

* cited by examiner

METHODS AND COMPOSITIONS FOR NUCLEIC ACID SAMPLE PREPARATION

CROSS-REFERENCE TO RELATED APPLICATIONS

This application is a continuation of U.S. patent application Ser. No. 12/383,855, filed Mar. 27, 2009, now U.S. Pat. No. 8,236,499, which claims the benefit of U.S. Provisional Patent Application 61/072,160, entitled, "Methods, Compositions, and Systems for Nucleic Acid Sample Preparation," by Patel, Bjornson, Travers, and Heiner, filed Mar. 28, 2008, the disclosures of both of which are incorporated herein by reference in their entireties for all purposes.

This application is also related to U.S. patent application Ser. No. 12/413,258, filed Mar. 27, 2009, now U.S. Pat. No. 8,153,375; and U.S. patent application Ser. No. 12/413,226, filed Mar. 27, 2009, now U.S. Pat. No. 8,143,030, all of which are incorporated herein by reference in their entireties for all purposes.

FIELD OF THE INVENTION

This invention is in the field of nucleic acid sequencing, particularly the preparation of templates for nucleic acid sequencing.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs and improve accuracy (See, e.g., Chan, et. al. (2005) "Advances in Sequencing Technology" (Review) Mutation Research 573: 13-40, Levene et al. (2003) "Zero Mode Waveguides for Single Molecule Analysis at High Concentrations," Science 299: 682-686).

Methods of preparing templates for large-scale sequencing projects have typically entailed constructing shotgun libraries that comprise overlapping fragments of, e.g., a genomic DNA; transforming cells with the library; growing cells to amplify each library member; and isolating and purifying library DNA. For example, shotgun cloning was initially used to prepare nucleic acid templates for sequencing small genomes such as that of the cauliflower mosaic virus (CMV) (Gardner, et al. (1981) "The complete nucleotide sequence of an infectious clone of cauliflower mosaic virus by M13mp7 shotgun sequencing." NAR 9: 2871-2888). More recently, this template preparation strategy has been used to produce templates for the sequencing of complex genomes, including the mouse, Drosophila, and human genomes (Mural, et al. (2001) "A comparison of whole-genome shotgun-derived mouse chromosome 16 and the human genome." Science 296: 1661-1671; Adams, et al. (2000) "The genome sequence of Drosophila melanogaster." Science 287: 2185-95; Venter, et al. (2001) "The Sequence of the Human Genome." Science 291: 1304-1351).

However, the cloning and cell culture techniques used in shotgun library construction methods are time consuming, labor-intensive, costly, and not easily amenable to automation. Purification protocols that are used to isolate cloned nucleic acid templates from cells, e.g., bacterial cells, for sequencing do not reliably produce nucleic acid samples that are sufficiently free of sequencing reaction inhibitors such as salts, carbohydrates and/or proteins. Furthermore, these disadvantages are exacerbated when conventional template preparation methods are scaled to the quantities that would be useful for high throughput sequencing technologies, e.g., single-molecule real-time (SNRT) sequencing systems, such as those described in, e.g., Levene et al. (2003) "Zero Mode Waveguides for single Molecule Analysis at High Concentrations," Science 299: 682-686; and Eid, et al. (2009) "Real-Time DNA Sequencing from Single Polymerase Molecules." Science 323: 133-138.

Consequently, there is an increasing demand for efficient, low-cost methods for the preparation of high-quality nucleic acid templates for next generation sequencing technologies. The present invention provides methods and compositions that would be useful for supplying high throughput DNA sequencing systems with such templates.

SUMMARY

The present invention provides methods and compositions that can be useful for supplying high throughput DNA sequencing systems with nucleic acid templates. The methods circumvent the need for expensive, labor-intensive library construction and cell culture methods and can be scaled to accommodate template production for a variety of high-throughput sequencing applications, including, e.g., sequencing large genomes, gene expression profiling (Spinella, et al. (1999) "Tandem arrayed ligation of expressed sequence tags (TALEST): a new method for generating global gene expression profiles." Nucleic Acids Res 27: e22, Velculescu, et al. (1995) "Serial analysis of gene expression." Science 270: 484-487), genome-wide methylation analysis, and microbiome analysis. The methods and compositions provided by the invention can be used to produce either linear or single-stranded nucleic acid loops.

Thus in a first aspect, the invention provides methods of producing a population of single-stranded nucleic acids. In the first set of methods, a genomic DNA, a cDNA, or a DNA concatamer is provided, and double-stranded fragments that comprise first exonuclease-sensitive strands and second exonuclease-resistant strands are generated from the genomic DNA, the cDNA, or the concatamer. The methods include eliminating the exonuclease-sensitive strands of the double-stranded fragment to produce the population of single-stranded nucleic acids. The genomic DNA, the cDNA, or the concatamer provided for any of the methods described herein can be derived from any of a variety of sources, e.g., a eukaryote, a prokaryote, an archaea, a virus, a phage, etc.

In certain embodiments, generating double-stranded fragments that comprise first exonuclease-sensitive strands and second exonuclease-resistant strands can comprise cleaving the genomic DNA, cDNA, or concatamer, e.g., via enzymatic digestion, sonication, mechanical shearing, electrochemical cleavage, and/or nebulization, to produce linear double-stranded nucleic acids. In these embodiments, exonuclease-sensitive tags can be ligated to the 5' ends of the first strands of the double-stranded nucleic acids and exonuclease-resistant tags can be ligated to the 5' ends of the second strands of the double-stranded nucleic acids to produce double stranded fragments with first exonuclease-sensitive strands and second exonuclease-resistant strands. The tags can optionally comprise one or more fluorescent label, blocking group, phosphorylated nucleotide, phosphorothioated nucleotide, biotinylated nucleotide, methylated nucleotide, nucleotide analog, uracil, sequence capable of forming a secondary structure, oligonucleotide hybridization site, restriction site, DNA promoter, RNA promoter, sample or library identification sequence, and/or cis regulatory sequence.

Optionally, producing the double stranded fragments with first exonuclease-sensitive strands and second exonuclease-resistant strands can comprise annealing a population of primer pairs, which comprise a first primer that comprises an exonuclease-sensitive 5' end and a second primer that comprises an exonuclease-resistant 5' end, to subsequences of the genomic DNA, the cDNA, or the concatamer. The primers can be extended with a polymerase to produce the double stranded fragments with first exonuclease-sensitive strands and second exonuclease-resistant strands. The primers can optionally comprise any of the moieties and/or sequences that can be included in the tags.

Those of skill in the art will appreciate that double-stranded nucleic acid fragments that comprise one exonuclease-sensitive strand and one exonuclease-resistant strand can be prepared using a variety of techniques well known in the art and that the embodiments described above should not be taken as limiting.

Producing a population of linear single-stranded nucleic acids from the double-stranded nucleic acid fragments that comprise first exonuclease-sensitive strands and second exonuclease-resistant strands can optionally include eliminating the exonuclease sensitive strand from each double-stranded fragment, e.g., via exonuclease digestion.

Compositions provided by the invention, related to the methods described above, comprise an exonuclease and a population of double-stranded nucleic acid fragments that comprise first exonuclease-sensitive strands and second exonuclease-resistant strands. The nucleic acid fragments of the composition, which can be derived from any of the sources described above, can optionally comprise overlapping subsequences of a genomic DNA, a cDNA, or a DNA concatamer. In preferred embodiments of the compositions, the genomic DNA, cDNA, or DNA concatamer are derived from a eukaryote. The fragments in the compositions can optionally comprise any one or more of the moieties that can be included in the tags.

The invention also provides methods of preparing closed single-stranded nucleic acid loops. One set of methods for preparing closed single-stranded loops includes providing a genomic DNA, a cDNA or a DNA concatamer, and generating double-stranded fragments that comprise first strands, e.g., exonuclease-sensitive strands, and second strands, e.g., exonuclease-resistant strands, from the genomic DNA, the cDNA, or the concatamer. The methods include separating the first strands of the double-stranded fragments from the second strands to produce single-stranded fragments, and circularizing the single-stranded fragments to produce the closed single-stranded nucleic acid loops.

The genomic DNA, the cDNA, or the concatamer from which the closed single-stranded nucleic acid loops are produced can optionally be derived from any of the sources described above. The population of double-stranded fragments that comprise first strands (or exonuclease-sensitive strands) and second strands (or exonuclease-resistant strands) can optionally be produced using any of the strategies described above. Separating the first strands from the second strands of the double-stranded fragments can optionally comprise digesting the first strands, e.g., exonuclease sensitive strands, of the fragments with an exonuclease to produce the single-stranded fragments.

Circularizing the single-stranded fragments to produce the closed single-stranded nucleic acid loops can optionally comprise annealing single-stranded nucleic acid splints to the single-stranded fragments. A splint can optionally be about 18-40 nucleotides long, and the single-stranded nucleic acid that is to be circularized can be about 100 nucleotides long. The first ends of the splints can optionally comprise first nucleotide sequences complementary to second nucleotide sequences at the first ends of the single-stranded fragments, and the second ends of the splints can optionally comprise third nucleotide sequences complementary to fourth nucleotide sequences at the second ends of the single-stranded fragments. Thus, annealing the splints to the single-stranded nucleic acids can bring the first and the second ends of each single-stranded fragment into proximity with one another. The first and the second ends of the single-stranded fragments can then be ligated to one another, producing the closed single-stranded nucleic acid loops. The splint can optionally be removed, e.g., via exonuclease digestion, e.g., before using the single-stranded nucleic acid loops in sequencing reactions.

The invention also provides compositions related to these methods of producing single-stranded nucleic acids loops. These compositions comprise a plurality of single-stranded nucleic acid fragments derived from overlapping subsequences of a genomic DNA, a cDNA, or a DNA concatamer, and a population of single-stranded nucleic acid splints. In the compositions, first ends of the splints are annealed to first ends of the fragments and second ends of the splints are annealed to seconds end of the fragments, circularizing each fragment by bringing its ends within proximity of one another. In preferred embodiments, the genomic DNA, cDNA or concatamer is derived from a eukaryote. The single stranded nucleic acids can optionally comprise any one or more of the moieties that can be included in nucleic acid tags. Optionally, the compositions can include a ligase.

The invention also provides additional methods of producing closed single-stranded nucleic acid loops. These methods include providing a genomic DNA, a cDNA, or a DNA concatamer, as described above, and generating double-stranded nucleic acid fragments with first strands that comprise a gap site from the genomic DNA, cDNA, or concatamer. These double-stranded fragments can be circularized to form double-stranded loops that comprise first non-contiguous strands and second contiguous strands. The first non-contiguous strands can be removed from the double-stranded loops to produce the population of closed single-stranded nucleic acid loops. Optionally, the methods include sequencing the single-stranded nucleic acid loops.

The genomic DNA or the cDNA from which fragments are generated can optionally be derived any of the sources described above. A gap site can be introduced into a nucleic acid strand using a variety of methods known in the art. The double-stranded fragments that comprise a gap site can optionally be generated by the strategies described previously. The gap site can optionally comprise an unphosphorylated 5' end or a sequence recognized by a nicking enzyme, e.g., a uracil-DNA glycosylase (UDG), a uracil-DNA N-glycosylase (UNG), or a site-specific restriction endonuclease engineered to cut one strand.

In embodiments wherein the gap site comprises an unphosphorylated 5' end, circularizing the double-stranded nucleic acid fragments to produce a population of double-stranded loops that comprise first non-contiguous strands and second contiguous strands can optionally comprise ligating first ends of the fragments to second ends of the fragments. Optionally, in embodiments wherein the gap site comprises a sequence recognized by a nicking enzyme, producing a population of double-stranded loops that comprise first non-contiguous strands and second contiguous strand can include ligating first ends of the fragments to second ends of the fragments and cleaving the strands that comprise the gap site with, e.g., a nicking enzyme that specifically recognizes the gap site, e.g., a UNG, a UDG, or a site-specific restriction endonuclease engineered to cut one strand. Removing first non-contiguous strands from the double-stranded loops can comprise digesting the non-contiguous strand with, e.g., an exonuclease, to produce the population of single-stranded nucleic acid loops.

Compositions related to these methods of producing single-stranded nucleic acid loops are also provided by the invention. The compositions comprise a plurality of double-stranded nucleic acid loops that comprise first non-contiguous strands and second contiguous strands. The loops of the composition comprise overlapping sequences of a genomic DNA, a cDNA, or DNA concatamer. The source of the genomic DNA, cDNA, or DNA concatamer is not limited. However, in preferred embodiments of the compositions, the genomic DNA, cDNA, or DNA concatamer is derived from a eukaryote. The double-stranded nucleic acid loops can optionally comprise any one or more of the moieties that can be included in the tags. Optionally, the compositions can comprise an exonuclease.

In other embodiments, single-stranded nucleic acid loops can also be produced by providing a genomic DNA, a cDNA, or a DNA concatamer, e.g., derived from any of the sources described above, and generating a population of double-stranded fragments that comprise first sacrificial strands with a rolling-circle replication (RCR) protein recognition sequence and second target strands. These methods include copying target strands of the double-stranded fragments to produce a population of single-stranded copies, and circularizing the single-stranded copies to produce the population of closed single-stranded nucleic acid loops.

The double-stranded fragments with first sacrificial strands with a rolling-circle replication (RCR) protein recognition sequence can optionally be generated as described previously. The RCR protein recognition sequence can optionally comprise a sequence that is bound by an RCR protein, optionally, an RCR protein that comprises a histidine-U-histidine-U-U-U amino acid motif, wherein U is a bulky hydrophobic amino acid residue, e.g., cisA.

Copying the target strands of the double-stranded fragments can comprise nicking sacrificial strands of the fragments, displacing the sacrificial strands, and replicating sequences of the target strands to produce the population of single-stranded copies. The sacrificial strands of the target strands can be nicked with an RCR protein, e.g., cisA, and displaced by a replisome, e.g., a replisome that comprises a single-stranded DNA binding protein (SSB), a helicase, a polymerase, and an RCR protein. Displacing the sacrificial strands can optionally comprise unwinding the sacrificial strands from the target strands of the double-stranded fragments with a replisome.

Replicating the target strand can comprise synthesizing nucleic acid strands that are complementary to the target strands to produce the population of single-stranded copies. Circularizing the single-stranded copies, e.g., the copied strands and the sacrificial strands, to produce the closed single-stranded nucleic acid loops can comprise ligating the ends of the copied strands and the sacrificial strands with an RCR initiation protein, e.g., cisA.

In a related aspect, compositions provided by the invention include a plurality of double-stranded nucleic acids, each of which comprise an overlapping subsequence of a genomic DNA, a cDNA, or a DNA concatamer. The double-stranded nucleic acids comprise a rolling-circle replication (RCR) protein recognition sequence, e.g., a sequence that is bound by an RCR protein, and optionally an RCR protein that comprises a histidine-U-histidine-U-U-U amino acid motif, wherein U is a bulky hydrophobic amino acid residue, e.g., cisA. The double-stranded nucleic acids of the composition can be closed loops or linear, and they can optionally comprise genomic DNA, a cDNA, or a DNA concatamer that is derived from a eukaryote. The nucleic acids of the compositions can optionally include any one or more of the moieties that can be included in tags.

The invention provides additional methods of producing a population of single-stranded linear nucleic acids that include providing a genomic DNA, a cDNA, or a DNA concatamer, and generating a population of double-stranded fragments from the genomic DNA, the cDNA, or the concatamer. The fragments generated in these methods have first strands with first ends that comprise a sequence that is recognized by a nicking enzyme. The methods include circularizing the double-stranded fragments to produce a set of closed double-stranded nucleic acid loops, cleaving sacrificial strands of the closed loops with the nicking enzyme to produce nicked loops, and copying target strands of the nicked loops to produce copied strands that comprise sequences that are recognized by the nicking enzyme. The copied strands are then nicked with the nicking enzyme to produce the single-stranded linear nucleic acids.

The genomic DNA, cDNA, or concatamer from which the double-stranded fragments are generated can optionally be derived from any of a variety of sources described previously, including, e. g., a eukaryote, a prokaryote, an archaea, a virus, a phage, etc. Methods of producing double-stranded fragments with first strands that comprise first ends with a sequence recognized by a nicking enzyme include, but are not limited to, any of the methods for generating double-stranded fragments that have been described previously.

Circularizing the double-stranded fragments can optionally comprise ligating the ends the fragments to produce closed loops. The sacrificial strands of the closed double-stranded loops can be optionally cleaved by an enzyme that recognizes the nicking sequence, e.g., a UNG, a UDG, or a site-specific restriction endonuclease engineered to cleave only one strand. One of skill in the art will recognize that the nicking enzyme used in these methods need not be limited to those listed above. Copying the target strands can optionally comprise displacing the sacrificial strands and copying the target strands, i.e., synthesizing nucleic acid strands that are complementary to the target strands, with, e.g., a strand-displacing polymerase, to produce the copied strands. Strand displacing polymerases optionally include, e.g., a PolI, a BstI, a Phi29, or a Phi29-like polymerases, such as those described in U.S. patent application Ser. No. 11/645,223, entitled POLYMERASES FOR NUCLEOTIDE ANALOGUE INCORPORATION, published Aug. 23, 2007 as Publication No. 2007-0196846. The copied strands can then be nicked with a nicking enzyme to produce the single-stranded linear nucleic acids. The nicking enzyme can optionally be any of the nicking enzymes described previously.

The invention also provides compositions that are related to these methods. Such compositions comprise a plurality of closed double-stranded nucleic acid loops that comprise overlapping fragments of a genomic DNA, a cDNA, or a DNA concatamer. Though the genomic DNA, the cDNA, or the DNA concatamer from which the loops have been generated can be derived from any source, in preferred embodiments, the loops comprise nucleic acids derived from a eukaryote.

The double-stranded loops of the compositions each comprise a sequence that is specifically recognized by enzymes that can introduce a nick in the sacrificial strands, e.g., those described above. Optionally, the loops in the compositions can comprise any one or more of the moieties that can be included in tags. The compositions can optionally comprise a nicking enzyme.

Methods for generating closed single-stranded nucleic acid loops can also include providing a genomic DNA, a cDNA, or a DNA concatamer, producing a population of double-stranded nucleic acid fragments from the genomic DNA, the cDNA, or the concatamer, providing first hairpin oligonucleotides to first ends of the nucleic acid fragments and providing second hairpin oligonucleotides to second ends of the nucleic acid fragments to generate the set of single-stranded nucleic acid loops. The first and second hairpins that are provided to the double-stranded fragments can optionally comprise identical nucleotide sequences and/or be the same length. In other embodiments, the first and second hairpins can comprise two different sequences and/or be two different lengths.

The genomic DNA, the cDNA, or the concatamer from which the closed single-stranded nucleic acid loops are produced can be derived from any of the previously described sources. The population of double-stranded nucleic acid fragments can be optionally generated according to strategies elaborated above.

Providing the double-stranded nucleic acid fragments with hairpin oligonucleotide segments can comprise annealing the first hairpin oligonucleotides to the first ends of the fragments, annealing the second hairpin oligonucleotides to the second ends of the fragments, and ligating the hairpin oligonucleotides to the ends of the fragments to generate the set of closed single-stranded nucleic acid loops that comprise regions of internal complementarity. Attaching the hairpins to the fragments can optionally comprise linking 5' strands of the first hairpins to 3' strands of the first ends of the fragments, linking 3' strands the first hairpins to 5' strands of the first ends of the fragments, linking 5' strands of the second hairpins to 3' strands of the second ends of the fragments, and linking 3' strands of the second hairpins to 5' strands of the second ends of the fragments to form a population of closed single-stranded nucleic acid loops.

The first hairpins can optionally comprise first single-stranded terminal sequences that are complementary to second single-stranded terminal sequences at the first ends of the fragments, and the second hairpins can optionally comprise third single-stranded terminal sequences that are complementary to fourth single stranded terminal sequences at the second ends of the fragments. The first or second hairpins can optionally comprise or encode one or more ligand, fluorescent label, blocking group, phosphorylated nucleotide, phosphorothioated nucleotide, biotinylated nucleotide, methylated nucleotide, nucleotide analog, uracil, sequence capable of forming a secondary structure, oligonucleotide hybridization site, restriction site, DNA promoter, RNA promoter, sample or library identification sequence, and/or cis regulatory sequence.

Compositions comprising first hairpin oligonucleotides, second hairpin oligonucleotides, and a plurality of double-stranded nucleic acid fragments that comprise overlapping subsequences of a genomic DNA, a cDNA, or a DNA concatamer, are provided by the invention. The genomic DNA, cDNA, or DNA concatamer can optionally be derived from any of the sources described previously. However, in preferred embodiments, the fragments of the composition are derived from a eukaryote.

The first or second hairpins of the compositions can optionally comprise or encode any of the moieties described previously. The first and second hairpins can optionally comprise the same sequence of nucleotides. In some embodiments of these compositions, the first and second hairpins can comprise two different nucleotide sequences. The first hairpins of the compositions can optionally comprise first single-stranded terminal sequences complementary to second single-stranded terminal sequences at the first ends of the fragments, and the second hairpins of the composition can optionally comprise third single-stranded terminal sequences complementary to fourth single stranded terminal sequences at the second ends of the fragments. The compositions can optionally include a ligase.

Linear single-stranded nucleic acids can be produced by another set of methods provided by the invention. This set of methods includes providing a genomic DNA, a cDNA, or a DNA concatamer, generating a set of double-stranded nucleic acid fragments from the genomic DNA, the cDNA, or the concatamer, and nicking sacrificial strands of the double-stranded nucleic acid fragments to produce nicked fragments. In these methods, the sacrificial strands are displaced from the fragments, and sequences between nick sites and ends on un-nicked strands that are exposed by the displacement of the sacrificial strands are copied with a strand displacing polymerase to produce the linear single-stranded nucleic acids.

The genomic DNA, the cDNA, or the concatamer from which the fragments are generated can optionally be derived from a eukaryote or any of the other sources described above. The double-stranded fragments can optionally be generated using any of the methods described above. Nicking the sacrificial strands of the fragments can optionally comprise cleaving the sacrificial strands with a nicking enzyme, such as a UDG, a UNG, or a site-specific restriction endonuclease engineered to cleave only one strand, to produce the nicked fragments. Displacing the sacrificial strands can optionally comprise removing the sacrificial strands from the un-nicked strands with a strand-displacing polymerase, e.g., those described above. The exposed sequences can be copied by replicating sequences between the nick sites and the ends on the un-nicked strands with the strand-displacing polymerase. Replicating can optionally comprise synthesizing nucleic acid strands that are complementary to the un-nicked strands, to produce the linear single-stranded nucleic acids.

Any of the preceding methods of generating closed single stranded nucleic acid loops or single-stranded nucleic acid fragments can further include the step of sequencing the single-stranded nucleic acids, e.g., in a high-throughput sequencing system, such as an array of zero-mode waveguides (ZMWs). In addition, any of the compositions described herein can optionally include any compound or molecule useful for sequencing including, but not limited to, e.g., a DNA polymerase, a buffer solution and/or salt solution, including, e.g., divalent metal ions, i.e., $Mg^{2+}$, $Mn^{2+}$, $Ca^{2+}$ and/or $Fe^{2+}$. Optionally, any of the compositions can be present in a ZMW.

Those of skill in the art will appreciate that the methods and compositions provided by the invention can be used alone or in combination. Systems that include modules for the production and/or sequencing of linear single-stranded nucleic acids and/or closed single-stranded nucleic acid loops are also a feature of the invention. Such systems can optionally include detectors, array readers, excitation light sources, one or more output devices, such as a printer and/or a monitor to display results, and the like.

Kits are also a feature of the invention. The present invention provides kits that incorporate the compositions of the invention, optionally with additional useful reagents such as one or more enzymes that are used in the methods, e.g., an\ nicking enzyme, a DNA polymerase, an RCR protein, etc., that can be unpackaged in a fashion to enable their use. Depending upon the desired application, the kits of the invention optionally include additional reagents, such as a control nucleic acids, buffer solutions and/or salt solutions, including, e.g., divalent metal ions, i.e., $Mg^{2+}$, $Mn^{2+}$, $Ca^{2+}$ and/or $Fe^{2+}$, to prepare the single-stranded nucleic acids produced by the methods for sequencing, e.g., in a high-throughput sequencing system. Such kits also typically include a container to hold the kit components, instructions for use of the compositions, and other reagents in accordance with the desired application methods.

DETAILED DESCRIPTION

Figure 1:
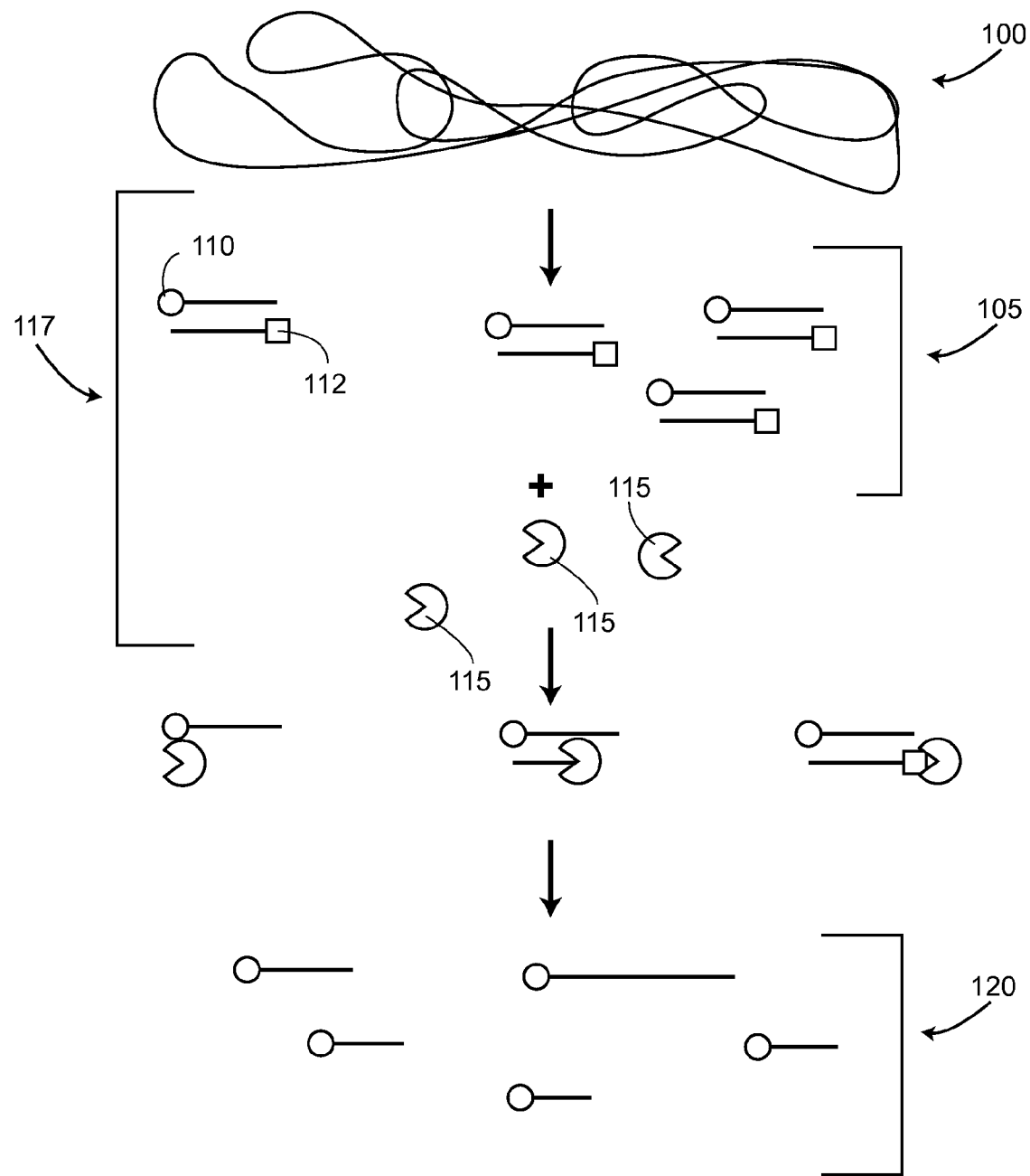
FIG. 1 illustrates methods and compositions for generating single-stranded nucleic acid fragments from double-stranded fragments.

Collecting reliable sequence data using high-throughput sequencing technologies depends in part on the availability of methods for the rapid and efficient production of high-quality nucleic acid templates. However, many of the methods of template preparation that are currently available entail constructing a library to clone, e.g., overlapping fragments of a genomic DNA, and growing cells to amplify each member of the library. These steps can be both time-consuming and expensive, and they can grow even more so when, e.g., a large genome is to be sequenced. The present invention provides methods and compositions that can be useful in supplying templates to such high throughput DNA sequencing systems as, e.g., single-molecule real-time (SMRT) systems and others. The methods circumvent the need for costly, labor-intensive cloning and cell culture methods, which can limit sample production from matching the capacities of modern sequencing systems (such systems are reviewed in, e.g., Chan, et al. (2005) "Advances in Sequencing Technology" *Mutation Research* 573: 13-40, and described in Levene et al. (2003) "Zero Mode Waveguides for Single Molecule Analysis at High Concentrations," *Science* 299: 682-686). Accordingly, a reduction in sequencing costs from current levels is a benefit of using the improved template preparation methods provided herein. Advantageously, the methods can be scaled to accommodate template production for a variety of sequencing applications, e.g., sequencing individuals' genomes, gene expression profiling (Spinella, et al. (1999) "Tandem arrayed ligation of expressed sequence tags (TALEST): a new method for generating global gene expression profiles." *Nucleic Acids Res* 27: e22, Velculescu, et al. (1995) "Serial analysis of gene expression." *Science* 270: 484-487), genome-wide methylation analysis, microbiome analysis, and others.

The methods and compositions provided by the invention can be used to produce either linear single-stranded nucleic acids or closed single-stranded nucleic acid loops. Single-stranded templates are typically preferable to double-stranded nucleic acids for sequencing because the thermodynamic stability of, e.g., homoduplex DNA, can promote the rapid reannealing of, e.g., double-stranded DNA that has been denatured in preparation for a sequencing reaction. Such reannealing reduces the efficiency with which a primer can hybridize to a template. Furthermore, the reannealing of double-stranded DNA can also impede polymerase-catalyzed extension of a sequencing reaction, decreasing the speed of the reaction and the accuracy of the results.

The invention provides a variety of methods and compositions related to the production of linear single-stranded nucleic acids or closed single-stranded nucleic acid loops, e.g., for sequencing. For example, in one embodiment, linear single stranded nucleic acids are produced from double stranded fragments that comprise an exonuclease-resistant strand and an exonuclease-sensitive strand. In a second embodiment, closed, single-stranded nucleic acid loops are produced from double stranded fragments using short nucleic acid splints. In a third embodiment, closed, single-stranded nucleic acid loops are produced from double stranded fragments that comprise one strand with a gap site. In another embodiment, replisomes comprising a rolling-circle replication protein are used to generate closed, single-stranded nucleic acid loops from double-stranded fragments that comprise one strand with a rolling circle replication (RCR) protein recognition sequence. In an another embodiment, strand-displacing polymerases are used to generate single-stranded linear nucleic acids from double-stranded fragments that comprise one strand with a sequence recognized by a nicking enzyme. In another embodiment provided by the invention, single-stranded nucleic acid loops are produced from self-annealing hairpin oligonucleotides that are attached to the ends of double-stranded nucleic acid fragments. Lastly, the invention provides methods of using a strand-displacing polymerase to generate single-stranded linear nucleic acids from double-stranded nucleic acid fragments that comprise one non-contiguous strand.

The detailed description is organized to first elaborate the various methods and compositions provided by the invention for the preparation of templates for high-speed, high-capacity sequencing platforms. Next, details regarding sequencing reactions and high-throughput sequencing systems are described. Broadly applicable molecular biological techniques that can be used to perform any of the methods are described thereafter.

Methods and Compositions for Generating Single-Stranded Nucleic Acid Fragments from Double-Stranded Nucleic Acid Fragments The methods and compositions described below are related to preparing linear single-stranded nucleic acids and can be used to supply high-throughput sequencing systems with templates in an efficient, timely, and cost-effective manner. Unlike shotgun cloning strategies for template preparation, the methods do not require library construction or cell culture, which can become impracticable if scaled to the degree necessary to meet the capacity of high-speed next generation sequencing platforms. Advantageously, the methods below produce single-stranded templates. Double-stranded templates can reanneal in a sequencing reaction, reducing primer annealing efficiency and impeding the polymerase-catalyzed extension of a sequencing reaction.

The methods entail providing a genomic DNA, a cDNA, or a DNA concatamer and producing double-stranded fragments that comprise one exonuclease-sensitive strand and one exonuclease-resistant strand. As used herein, a "DNA concatamer" refers to a long DNA molecule comprising a multiplicity of short sequence tags, e.g., derived from expressed transcripts, that have been linked in tandem. Such concatamers can be used in genome-wide expression profiling. The exonuclease-sensitive strands of each double-stranded fragment are then eliminated, producing a population of linear, single-stranded nucleic acid fragments.

These methods are schematically illustrated in FIG. 1. In a first step, genomic DNA, cDNA or a DNA concatamer 100, is provided. The genomic DNA, cDNA, or concatamer can be derived from any of a variety of sources, including prokaryotes, archaea, viruses, phage, eukaryotes, etc. In preferred embodiments of the methods, the genomic DNA, cDNA or concatamer is derived from a eukaryote, such as a human or other mammal with a complex genome.

In the next step, population of double-stranded nucleic acid fragments 105 is generated from the genomic DNA, cDNA, or concatamer 100. The double-stranded fragments, which are preferably between about 100 and 2000 base pairs long, comprise exonuclease-sensitive strands 112 and exonuclease-resistant strands 110.

Population of fragments 105 can be generated using any of a variety of techniques well known in the art. For example, the genomic DNA, cDNA, or concatamer can be cleaved, e.g., via enzymatic digestion, sonication, mechanical shearing, electrochemical cleavage, and/or nebulization. Following the fragmentation of the genomic DNA, cDNA, or concatamer, exonuclease-sensitive tags 112 can be attached to the 5' ends of the first strands of the fragments and exonuclease-resistant tags 110 can be attached to the 5' ends of the second strands of the fragments, e.g., with a ligase, via primer extension, via chemical linkage, and the like. Optionally, the double-stranded fragments can be produced by annealing a population of nested primer pairs, e.g., which pairs comprise one primer that comprises an exonuclease-sensitive 5' end and a second primer that comprises an exonuclease-resistant 5' end, to the genomic DNA, the cDNA or the concatamer, and extending the primers with a polymerase. Those of skill in the art will recognize that the methods of generating double stranded nucleic acid fragments comprising one exonuclease sensitive strand and one exonuclease resistant strand that are described above should not be taken as limiting.

As used herein, a "tag" refers to a moiety linked to a nucleic acid of interest that can be used as a molecular recognition site to identify or distinguish the nucleic acid in a population, e.g., as a means to permit a protein, e.g. a DNA-binding protein, or an enzyme, e.g., an exonuclease, a restriction enzyme, a nicking enzyme, or the like, to recognize the nucleic acid and perform an activity, and/or as a means by which to separate the nucleic acid from the population. A tag can comprise one or more of a number of moieties, including labeled or modified nucleotides, e.g., fluorescently labeled nucleotides, nucleotide analogs, or the like. Tags can also comprise specific nucleotide sequences, e.g., restriction sites, cis regulatory elements, recognition sites for nucleic acid-binding proteins, sequences capable of forming secondary structures, or the like. The tags and/or primers used in generating the double-stranded fragments that comprise first exonuclease-sensitive strands and second exonuclease-resistant strands can comprise one or more ligand, fluorescent label, blocking group, phosphorylated nucleotide, phosphorothioated nucleotide, biotinylated nucleotide, methylated nucleotide, nucleotide analog, uracil, a sequence capable of forming a secondary structure, oligonucleotide hybridization site, restriction site, DNA promoter, RNA promoter, sample or library identification sequence, cis regulatory sequence, and/or the like. For example, an "exonuclease resistant tag" can include a 5' phosphorylated nucleotide, which prevents the nucleic acid to which it is attached from being digested by a 5' exonuclease. An "exonuclease sensitive strand" can include a 5' unphosphorylated nucleotide, which renders the nucleic acid to which it is attached susceptible to digestion by a 5' exonuclease.

Following the production of double-stranded fragments that comprise exonuclease-sensitive strands 112 and exonuclease-resistant strands 110, the exonuclease-sensitive strands 112 are eliminated, e.g., via digestion with exonuclease 115, thereby producing single-stranded linear nucleic acid fragments 120 that can subsequently be sequenced in high-throughput sequencing systems (described elsewhere herein). The invention provides related composition 117 that includes an exonuclease and overlapping double-stranded fragments of a genomic DNA, cDNA, or concatamer that each comprise one exonuclease-sensitive strand and one exonuclease-resistant strand. The fragments can include any one or more of the moieties described previously.

Methods and Compositions for Generating Single-Stranded Nucleic Acid Loops from Double-Stranded Fragments The methods and compositions described below relate to preparing closed nucleic acid loops that can be used, e.g., in sequencing reactions in high-throughput sequencing systems. In contrast to shotgun cloning strategies for template preparation, these methods do not require library construction or cell culture, which are costly, time-consuming, and which can become impracticable if scaled to the degree necessary to meet the capacity of high-speed next generation sequencing platforms. Advantageously, the methods below produce single-stranded nucleic acid loops, which can be preferable in sequencing reactions. Double-stranded templates can reanneal, reducing primer annealing efficiency and impeding the polymerase-catalyzed extension of a sequencing reaction. In fact, loops can also be preferable to linear templates because a DNA polymerase can only copy a linear template, e.g., to which a primer has been annealed, once before it falls off the distal end of the template. In contrast, a strand-displacing polymerase can replicate a contiguous nucleic acid loop several times. The primer that is annealed to the loop is eventually displaced at its 5'-end upon completion of one revolution of the polymerase around the nucleic acid loop, and as polymerization and displacement continue, a linear, single-stranded product comprising several copies of the nucleic acid sequence of the loop is generated. Accordingly, using nucleic acid loops in sequencing can provide an internal sequencing control.

The methods for preparing closed, single-stranded nucleic acid loops include providing a genomic DNA, a cDNA, or a DNA concatamer and generating double-stranded fragments that each comprise a first strand (e.g., an exonuclease sensitive strand) and a second strand (e.g., an exonuclease resistant strand). In a following step, the two strands in each fragment are separated, and the resulting single-stranded fragments are circularized to produce closed single-stranded nucleic acid loops, which can then be used as templates in a high-throughput sequencing system.

Figure 2:
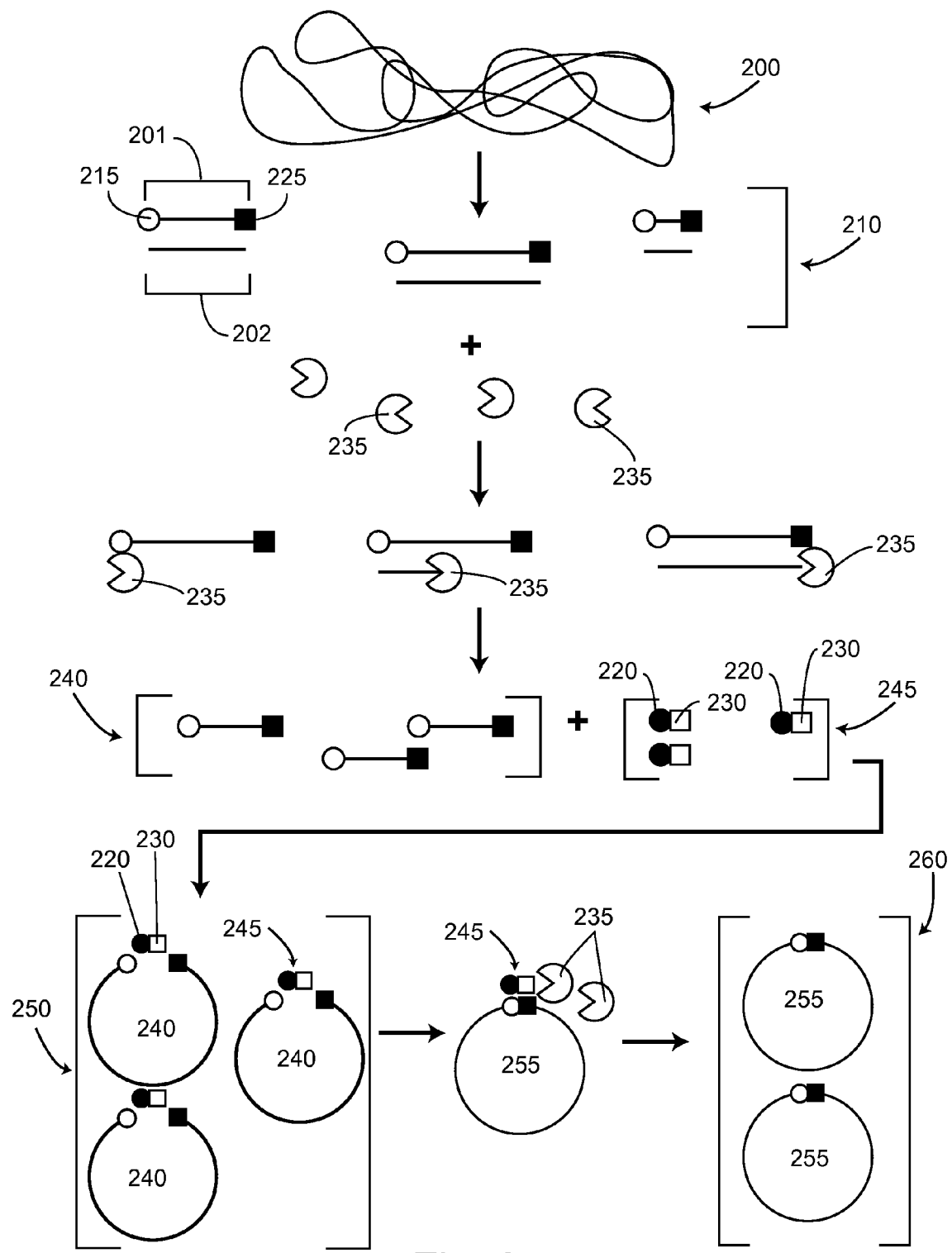
FIG. 2 illustrates methods and compositions related to generating closed single-stranded nucleic acid loops from double-stranded fragments.

FIG. 2 depicts a schematic for these methods. First, population of double-stranded nucleic acid fragments 210, which comprise first strands (or exonuclease-sensitive strands) 202 and second strands (or exonuclease-resistant strands) 201, are generated from genomic DNA, cDNA, or a DNA concatamer 200, using any of the strategies described previously. The genomic DNA, cDNA, or concatamer can be derived from any source known to those of skill in the art.

Next, strands 201 and 202 of the double-stranded fragments are separated from one another, e.g., via digestion with exonuclease 235 to produce set of single-stranded nucleic acid fragments 240 e.g., fragments that are about 100 to about 1000 base pairs long. Those of skill in the art will recognize that the strands of a double-stranded nucleic acid fragment can be separated using a variety of techniques that those described herein are not to be taken as limiting. Single-stranded fragments 240 can then be circularized to produce a population of single-stranded nucleic acid loops, e.g., for sequencing.

As used herein, "circularizing" a nucleic acid refers to the formation of a loop, e.g., a ring-like structure that does not intersect itself, from a linear nucleic acid fragment, e.g., a single-stranded fragment or double-stranded fragment. A linear nucleic acid fragment can be circularized by joining, e.g., ligating, the ends of the fragment to one another, e.g., to form a "closed loop" or "contiguous loop", wherein each nucleotide is covalently joined to the nucleotides preceding and following it, or by bringing the ends of the fragment into proximity with one another, e.g., to form a "non-contiguous loop", wherein at least two nucleotides of the fragment are not joined by a covalent bond.

Single-stranded fragments 240 can be circularized using any number of strategies. However, in a preferred embodiment, fragments 240 can be circularized using splints 245. As used herein, a "splint" refers to a short, single-stranded nucleic acid oligomer about 18-40 nucleotides long that comprises 3' sequences and 5' sequences that form a perfectly matched homoduplex when hybridized to the 5' and 3' sequences, respectively, at the ends of a second, preferably longer single-stranded nucleic acid molecule. Following hybridization to the longer single-stranded nucleic acid, the splint functions as a molecular bridge that circularizes the second nucleic acid molecule by holding its ends in apposition.

For example, splints 245 comprise first ends that comprise sequences 220 that are complementary to sequences 215 at the first ends of single-stranded nucleic acid fragments 240. Splints 245 also comprise second ends that comprise sequences 230 that are complementary to sequences 225 at the second ends of single-stranded fragments 240. Annealing fragments 240 to the splints 245 brings the two ends of each fragment within close proximity of one another (See, e.g., composition 250), which increases the efficiency of ligation, wherein the two ends of each fragment 240 are covalently linked, e.g., via enzymatic ligation. Splints 245 can be removed, e.g., via digestion with exonuclease 235, to produce single-stranded nucleic acid loops 255. Composition 260 can then be provided to a high-throughput sequencing system.

Methods of generating single-stranded nucleic acid loops have been described in Kuhn, et al. (2002) "Rolling-circle amplification under topological constraints." *NAR* 30: 574-580 for use in determining the efficiency of rolling-circle amplification using templates with varying topologically linked DNA constructs. However, because the methods in Kuhn et al. only produced a homogenous population of single-stranded nucleic acid loops, e.g., loops that each comprise the same sequence, they are not suitable for use in sequencing reactions. In contrast, the methods provided by the invention include the steps of fragmenting a genomic DNA, a cDNA, or a DNA concatamer to produce a heterogeneous population of nucleic acid loops that comprise overlapping sequences of the genomic DNA, cDNA, or concatamer. Accordingly, the heterogeneous templates can be sequenced to generate data that can be assembled to determine the nucleotide sequence of, e.g., a complex mammalian genome.

Methods of generating single-stranded nucleic acid loops for use in nucleic acid sequencing have also been described in United States Patent Publication No. US 2008/0213771 METHODS AND COMPOSITIONS FOR LARGE SCALE ANALYSIS OF NUCLEIC ACIDS USING DNA DELETIONS, by Drmanac. These methods entail generating linear single-stranded nucleic acids from a fragmented, denatured genomic DNA and ligating poly dA tails to 3-prime ends of the nucleic acids. This is then followed by ligation of the free ends intramolecularly with the aid of a splint, which splint is complementary to the poly dA tail at one end and complementary to any sequence at the other end by virtue of a segment of degenerate nucleotides. Whereas in the methods of 2008/0213771, single stranded linear nucleic acids that are to be circularized using a splint are generated by fragmenting and denaturing a genomic DNA, the single stranded linear nucleic acids, e.g., that are to be circularized, are generated, e.g., using the methods herein, by fragmenting a genomic DNA and digesting one strand of each double-stranded fragment. The thermodynamic stability of, e.g., homoduplex DNA, can promote the rapid reannealing of, e.g., double-stranded DNA fragments that have been denatured in preparation for circularization.

The invention also provides Composition 250, which is related to the present methods. Composition 250 comprises a population of single-stranded nucleic acid fragments 240, which comprise overlapping subsequences of a genomic DNA, a cDNA, or a DNA concatamer, and a population of single-stranded nucleic acid splints 245. In this composition, first ends 220 of the splints are annealed to first ends 215 of the fragments and second ends 230 of the splints are annealed to seconds ends 225 of the fragments, such that the two ends of each fragment are brought within proximity of one another. The genomic DNA, the cDNA, or the concatamer from which the single-stranded fragments in composition 250 can optionally be derived from, e.g., a eukaryote, a prokaryote, an archaebacterium, a phage, or a virus. The fragments in the composition can optionally comprise any one or more of the moieties described previously. Optionally, the composition can include a ligase.

In another embodiment, single-stranded nucleic acid loops are generated from double-stranded nucleic acid fragments, e.g., derived from a genomic DNA, a cDNA, or a DNA concatamer, that comprise a gap site. As described herein, a "gap site" is a nucleotide sequence or nucleotide-associated moiety, such as an unphosphorylated 5' C, that permits the introduction of a gap into a contiguous nucleic acid strand. For example, a gap site in a nucleic acid fragment can comprise an unphosphorylated 5' end or a sequence that is recognized by a nicking enzyme. As used herein, a "nicking enzyme" refers to an enzyme that can cleave one strand of a double-stranded nucleic acid. A nicking enzyme can optionally nick a nucleic acid strand at any location, or it can recognize a specific sequence and cleave a nucleic acid strand only at that sequence. Examples of nicking enzymes include, e.g., a UDG, a UNG, or a restriction endonuclease engineered to cleave only one strand of a double-stranded nucleic acid. Those of skill in the art will recognize that there exist myriad enzymes that can cleave a single strand of a double-stranded nucleic acid and that the enzymes listed above are not to be taken as limiting.

Next, the double stranded fragments are circularized to produce a population of double-stranded loops that comprise first strands (or non-contiguous strands) and second strands (or contiguous strands). The first (e.g., non-contiguous) strands of each double-stranded loop are then removed to produce a population of closed, single-stranded nucleic acid loops useful, e.g., in a high-throughput sequencing system. This method is schematically depicted in FIG. 3.

In FIG. 3, double stranded nucleic acid fragments wherein one strand includes a gap site, e.g., populations 305 and 350, can be generated as described previously or by methods well-known in the art. In one embodiment, double stranded fragments 350, comprising 5' unphosphorylated first strands 336 and 5' phosphorylated second strands 335, are produced from DNA, e.g., genomic DNA, cDNA, or concatamer 300. In this embodiment, the 5' unphosphorylated end of each first strand 336 in each fragment comprises the gap site. In an alternate embodiment, set of double-stranded fragments 305, which each comprise a first strand that encodes sequence 306, are generated from genomic DNA, cDNA, or concatamer 300. In this embodiment, sequence 306, which is recognized by nicking enzyme 315, comprises the gap site.

Figure 3A:
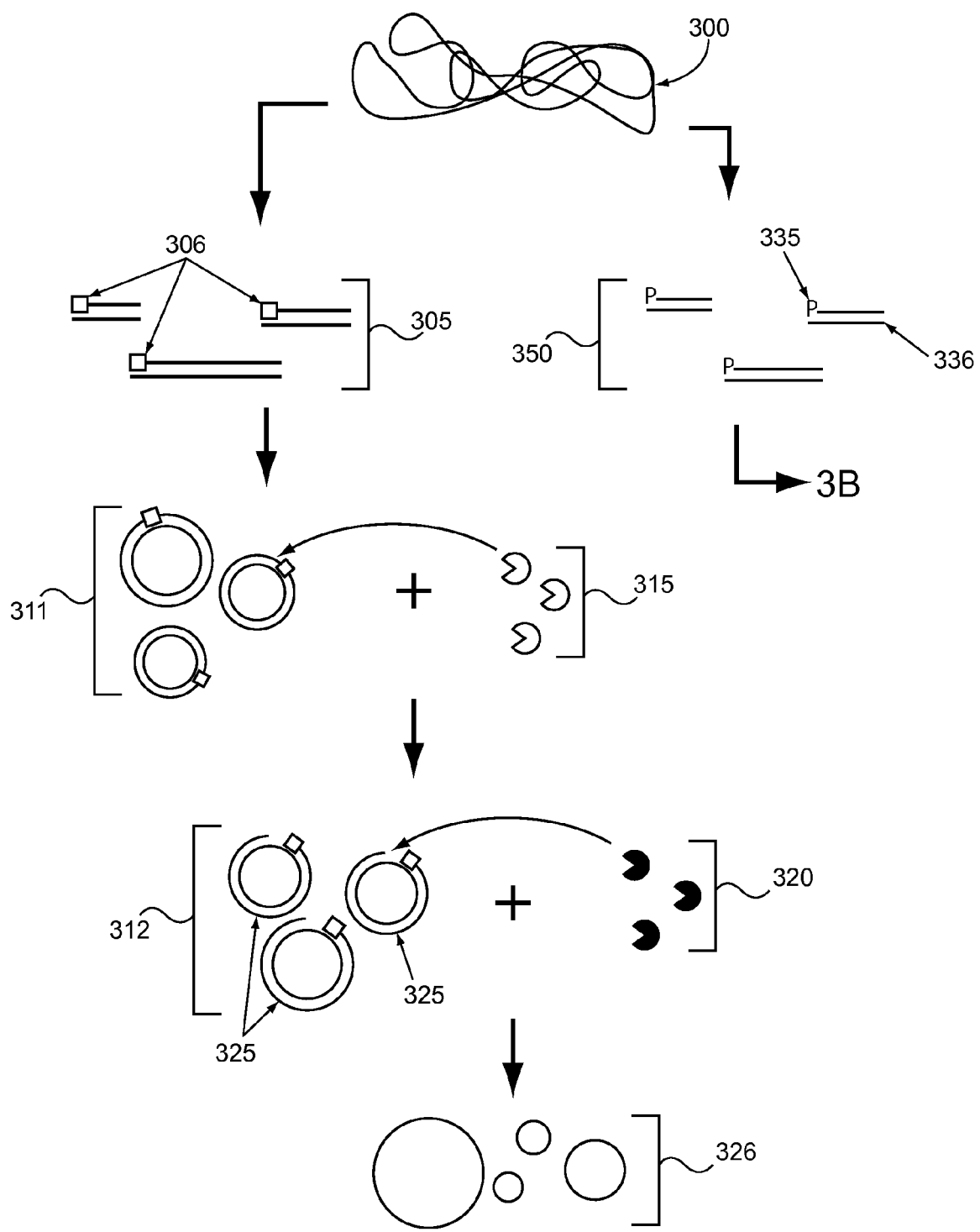
FIGS. 3A and 3B illustrate other methods and compositions related to producing closed single-stranded nucleic acid loops from double-stranded fragments.
Figure 3B:
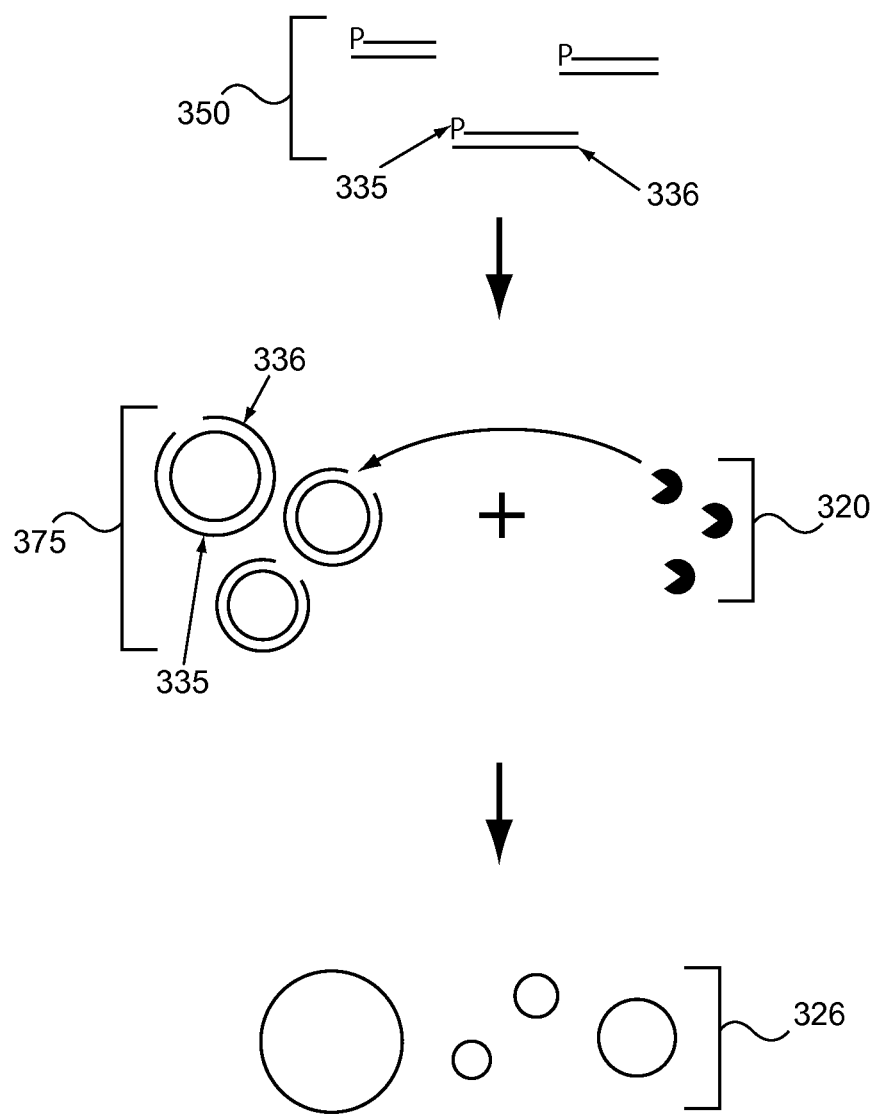

Fragments 350, which comprise 5' unphosphorylated first strands 336 and 5' phosphorylated second strands 335, can be circularized, e.g., with a ligase, to produce population of double-stranded loops 375 that each comprise first non-contiguous strands and second contiguous strands. (See FIG. 3B.) Alternately, fragments 305 can be circularized, e.g., with a ligase, to produce closed double-stranded closed loops 311. (See FIG. 3A.) The first strand of each double-stranded loop that encodes sequence 306 can then be cleaved with nicking enzyme 315 to produce population 312, which comprises double-stranded loops that comprise first non-contiguous strands 325 and second contiguous strands. The nicking enzyme used in this embodiment of the methods can be, e.g., a site-specific restriction endonucleases engineered to cleave only one strand. Alternately, the nicking can be uracil-DNA N-glycosylase (UNG), which cleaves uracil N-glycosylic bonds, or uracil DNA glycosylase (UDG), which catalyzes the release of free uracil from uracil-containing DNA. Those of skill in the art will appreciate that there exist a myriad of enzymes that can nick a single strand in double-stranded nucleic acid and that those described herein are not to be taken as limiting. As shown in FIGS. 3A and 3B, the non-contiguous strands, e.g., the first strands, of each double-stranded loop in populations 312 and 375 can then be removed, e.g., by digestion with exonuclease 320, to produce single-stranded nucleic acid loops 326 that can be used, e.g., in high-throughput sequencing systems.

Related composition 375 is provided by the invention. The composition comprises a set of double-stranded nucleic acid loops comprising overlapping fragments of a genomic DNA, a cDNA, or DNA concatamer derived from any of the sources described previously. The double-stranded nucleic acid loops of the composition each comprise one non-contiguous strand and one contiguous strand. The genomic DNA, cDNA, or concatamer present in the loops can optionally be derived from any of the previously described sources. The double-stranded nucleic acid loops can optionally comprise any one or more of the moieties described previously. Optionally, the composition can include an exonuclease.

Methods and Compositions for Producing Double-Stranded Linear Templates from Which Closed Single-Stranded Nucleic Acid Loops are Copied The invention also provides methods and compositions related to generating a population of double-stranded fragments, copying the fragments, and producing closed single-stranded loops from the copied fragments. The closed, single-stranded nucleic acid loops produced by these methods can be used to provide templates in high-throughput sequencing systems in, e.g., a time-efficient and cost-effective manner. Unlike shotgun cloning strategies for template preparation, these methods do not require library construction or cell culture, which are laborious, expensive, and not easily scalable to meet the capacities of next generation sequencing systems. Advantageously, the methods below produce closed single-stranded nucleic acid loops, which are preferable in sequencing reactions. For example, denatured double-stranded templates can rehybridize, reducing primer annealing efficiency and impeding the polymerase-catalyzed extension of a sequencing reaction.

Figure 4:
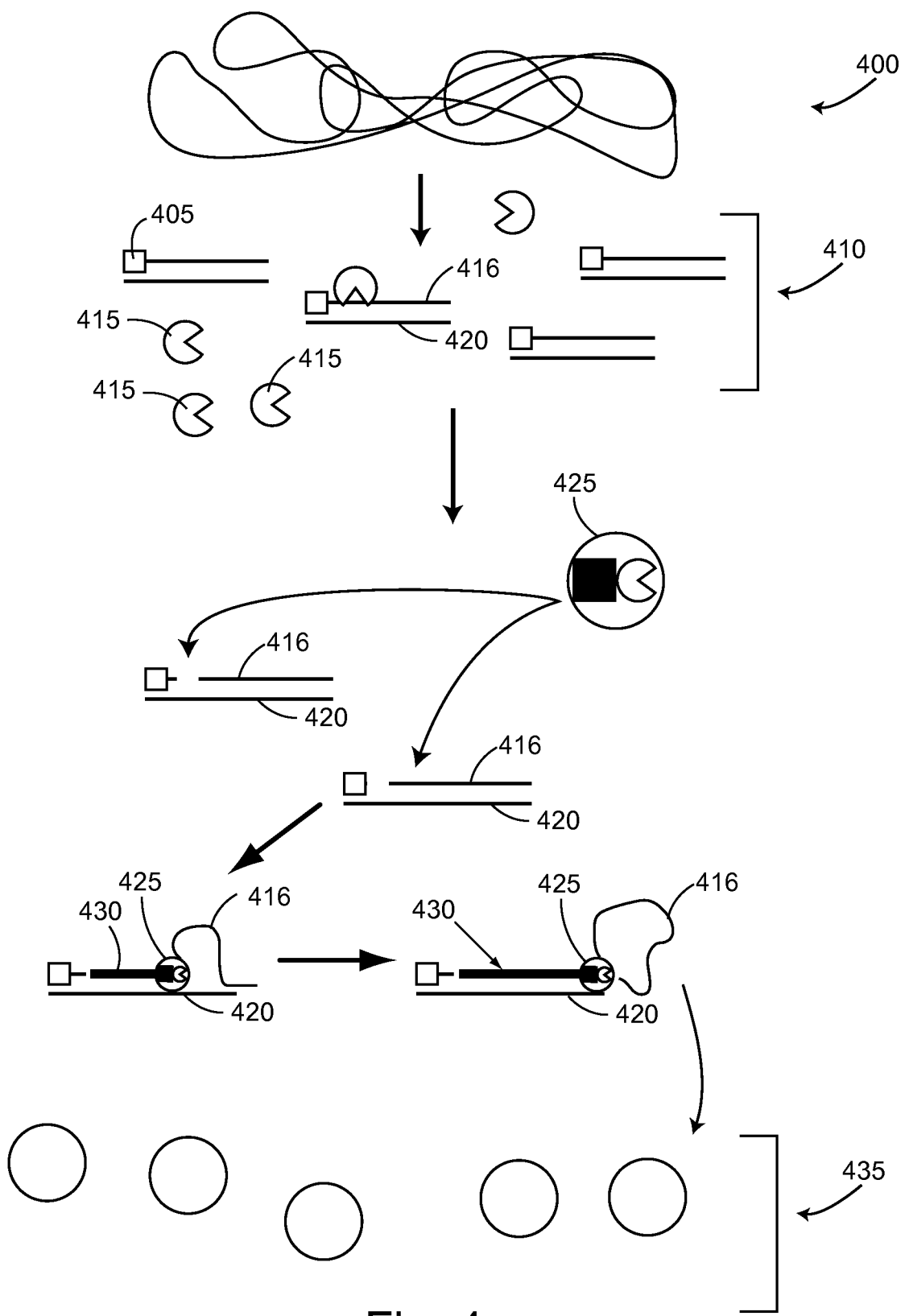
FIG. 4 illustrates additional methods and compositions related to generating closed single-stranded nucleic acid loops from double-stranded nucleic acids.

Double-stranded fragments that each comprise one strand that comprises a rolling-circle replication (RCR) protein recognition sequence are generated, e.g., using any of the strategies known in the art or described herein, e.g., from a genomic DNA, a cDNA, or a DNA concatamer derived from any of the sources described above. RCR protein recognition sequences are described in further detail in, e.g., Koonin, et al. (1993) "Computer-assisted dissection of rolling circle DNA replication." *BioSystems* 30: 241-268; and Novick (1998) "Contrasting Lifestyles of rolling-circle phages and plasmids." *TIBS* 23: 434-438. Next, target strands of each double-stranded fragment are copied to produce a population of single-stranded nucleic acid copies. As used herein, "copying" refers to the process of replicating a nucleic acid molecule to generate a new nucleic acid that comprises a sequence complementary to that of the original. The nucleic acids that are synthesized via copying are the "copied strands," and the rate of nucleotide misincorporation during the synthesis of the copied strands is assumed to be approximately <5%, or, more preferably, 0%. The copied strands are then circularized to produce a population of single-stranded nucleic acid loops, which can optionally be provided to a high-throughput sequencing system. This method is illustrated in FIG. 4.

Double-stranded nucleic acid fragments 410 are generated from genomic DNA, cDNA, or a DNA concatamer 400, as described above. Fragments 410 comprise target strands 420 and sacrificial strands 416. Sacrificial strands 416 each comprise rolling-circle replication (RCR) protein recognition sequence 405. As used herein, "target strands" refer to the strands in double strand nucleic acid molecules, e.g., linear nucleic acids or nucleic acid loops, that serve as templates from which new molecules are synthesized. "Sacrificial strands", as used herein for this method and other methods of the invention, refer to the strands in double-stranded nucleic acid molecules, e.g., linear nucleic acids or nucleic acid loops, that are cleaved and removed, e.g., via displacement or enzymatic digestion, to permit the copying of target strands to produce single-stranded nucleic acid molecules.

In a following step, target strands 420 of each of the double-stranded fragments in population 410 are repeatedly copied to produce single-stranded loops 435. In preferred embodiments, copying target strands 420 to produce single-stranded nucleic acid loops 435 includes nicking sacrificial strands 416 of each double-stranded fragment, e.g., with RCR protein 415. The RCR protein that nicks sacrificial strands 416 can optionally be an RCR protein that comprises a histidine-U-histidine-U-U-U amino acid motif, wherein U is a bulky hydrophobic amino acid, e.g., cisA.

Replisome 425, which generally comprises a single-stranded DNA-binding protein (SSB), a helicase, a polymerase, and an RCR protein, then displaces sacrificial strands 416 and copies sequences of target strands 420 that are exposed by the displacement of sacrificial strands 416. Further details regarding RCR replisomes can be found in, e.g., e.g., Koonin, et al. (1993) "Computer-assisted dissection of rolling circle DNA replication." *BioSystems* 30: 241-268; and Novick (1998) "Contrasting Lifestyles of rolling-circle phages and plasmids." *TIBS* 23: 434-438. In copying target strands 420, replisome 425 synthesizes single-stranded copies 430. The RCR protein in replisome 425 comprises an activity which permits it to then circularize single-stranded copies 430 (and sacrificial strands 416) to produce closed single-stranded nucleic acid loops 435.

It will be apparent to one of skill in the art that these methods can optionally include the step of circularizing population of fragments 410 to produce a population of double-stranded loops. The remaining steps can be performed using the double-stranded loops to generate population 435.

Composition 410, which is related to the present methods, is also an embodiment of the invention. Composition 410 comprises a population of double stranded nucleic acids derived from, a genomic DNA, a cDNA or a DNA concatamer. Each of the double-stranded nucleic acids in population 410 includes one strand that comprises an RCR protein recognition sequence. The nucleic acids of the composition 410 can optionally be closed loops or linear, and they can optionally be derived from a eukaryote. In some embodiments of this composition, the RCR protein recognition sequence comprises a sequence recognized by an RCR protein that comprises a histidine-U-histidine-U-U-U motif; wherein U is a bulky hydrophobic amino acid. Optionally, the RCR protein that recognizes the RCR protein recognition sequence can be a cisA protein. The double stranded nucleic acids in the composition can optionally comprise any one or more of the moieties described previously.

Methods and Compositions for Producing Closed Double-Stranded Loops from Which Linear Single-Stranded Nucleic Acids are Copied Methods of preparing templates for large-scale sequencing projects have typically entailed constructing shotgun libraries that comprise overlapping fragments of, e.g., a genomic DNA; transforming cells with the library; growing cells to amplify each library member; and isolating and purifying library DNA. However, template production can be scaled to the volumes that can be accommodated by high-throughput sequencing platforms using novel methods provided herein.

The present methods can be used to produce linear single-stranded nucleic acids. These methods not only circumvent cloning and cell culture steps, they also beneficially produce single-stranded nucleic acid templates, which are preferable in sequencing reactions.

In one embodiment, the methods include generating a population of double stranded fragments that comprise a sacrificial strand that encodes a sequence recognized by a nicking enzyme. The fragments are then circularized to produce closed double-stranded loops. Sacrificial strands in each loop are cleaved by a nicking enzyme, and the target strands of each loop are copied to produce copied strands that encode a sequence recognized by the nicking enzyme. The copied strands are then nicked to produce single stranded nucleic acids that can be used in a high-throughput sequencing systems.

Figure 5:
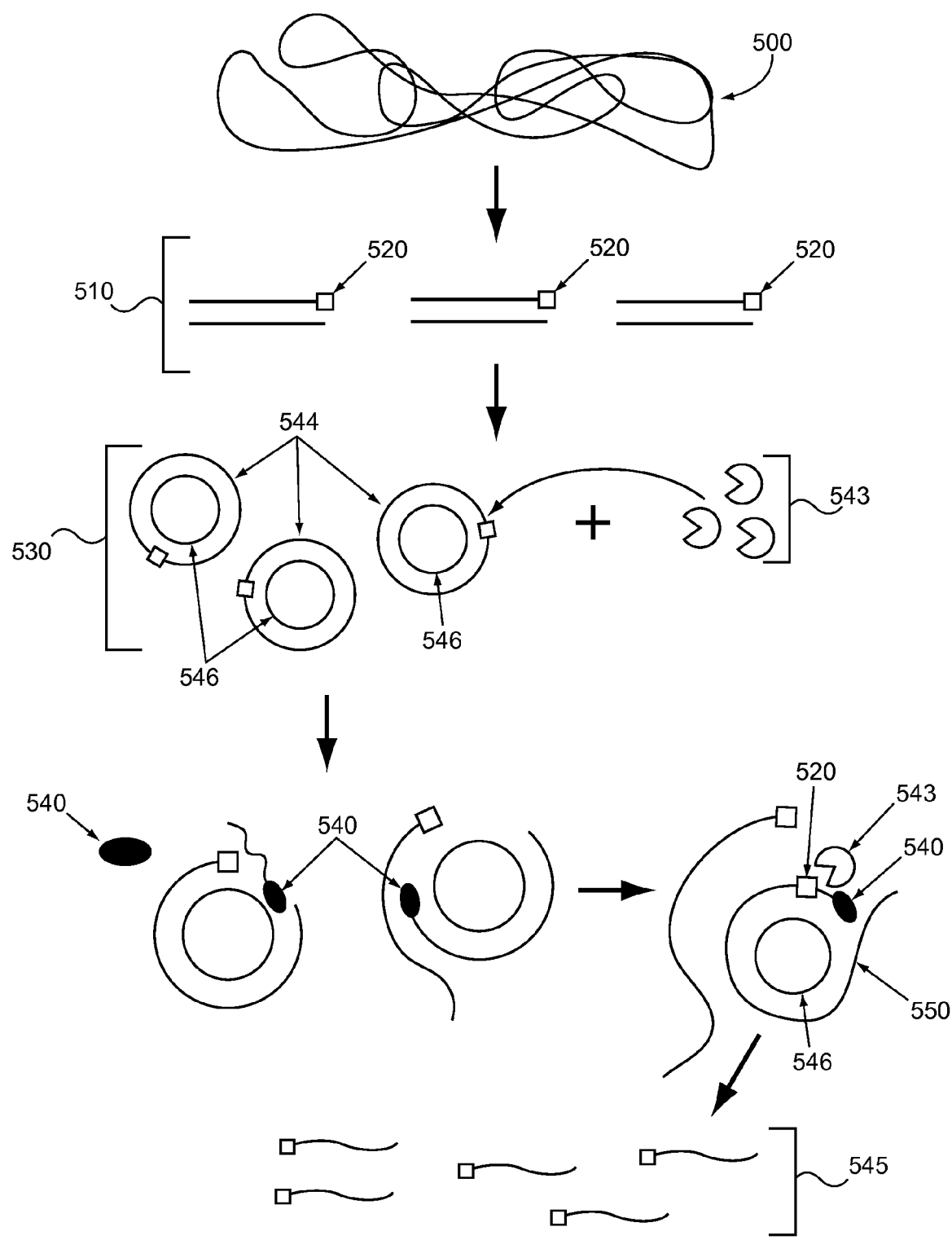
FIG. 5 illustrates methods and compositions for producing closed double-stranded nucleic acid loops from which linear single-stranded nucleic acids are copied.

In this set of methods, which are illustrated in FIG. 5, double-stranded nucleic acid fragments 510 are produced from genomic DNA, cDNA, or a DNA concatamer 500 using, e.g., any of the previously described strategies. Double-stranded fragments 510 each comprise a sacrificial strand that encodes sequence 520, which is recognized by nicking enzyme 543, e.g., a UNG, a UDG, or a site-specific restriction endonuclease engineered to cleave only one strand. The double-stranded fragments can be circularized, e.g., with a ligase, to produce a set of closed double-stranded loops 530. Sacrificial strands 544 of each double-stranded loop are cleaved by nicking enzyme 543, and displaced, e.g., by strand-displacing polymerase 540, which also copies target strands 546, thereby generating copied strands 550. Copied strands 550 are eventually displaced at their 5'-ends upon completion of one revolution of the target strand 546 by strand-displacing polymerase 540. As polymerization and displacement continue, copied strands 550, which each comprise the sequence that is recognized by nicking enzyme 543, are cleaved by nicking enzyme 543 to produce single-stranded nucleic acids 545.

The strand displacing polymerases that can be used in preferred embodiments of these methods include, e.g., PolI, BstI, Phi29, or Phi29-like polymerases, such as those described in U.S. patent application Ser. No. 11/645,223, entitled POLYMERASES FOR NUCLEOTIDE ANALOGUE INCORPORATION.

The invention provides composition 530, which is related to the methods above. Composition 530 comprises closed double-stranded nucleic acid loops that comprise overlapping subsequences of a genomic DNA, a cDNA, or a DNA concatamer. The loops include sequence sacrificial strands 544 that encode sequence 520, which is recognized by nicking enzyme 543. In preferred embodiments of the compositions, the closed double-stranded nucleic acid loops in composition 530 are derived from a eukaryotic genomic DNA, a eukaryotic cDNA, or concatamer comprising eukaryotic DNA. The double stranded nucleic acid loops can optionally comprise any one or more of the moieties described previously. The composition can optionally include a nicking enzyme, e.g., nicking enzyme 543.

Methods and Compositions for Generating Single-Stranded Nucleic Acid Loops from Double-Stranded Fragments and Hairpin Oligonucleotides There is an increasing demand for efficient, low-cost methods for the preparation of high-quality nucleic acid templates for next generation sequencing technologies. The methods and compositions described below can be useful for supplying high throughput DNA sequencing systems with such templates. The methods avoid labor-intensive, costly cloning and cell culture steps that are typically used in currently available strategies to generate nucleic acid templates for sequencing, e.g., shotgun cloning. Moreover, these methods beneficially produce single-stranded nucleic acids, which do not reduce primer annealing efficiency and impede the polymerase-catalyzed extension of a sequencing reaction due to reannealing of double-stranded templates.

Figure 6:
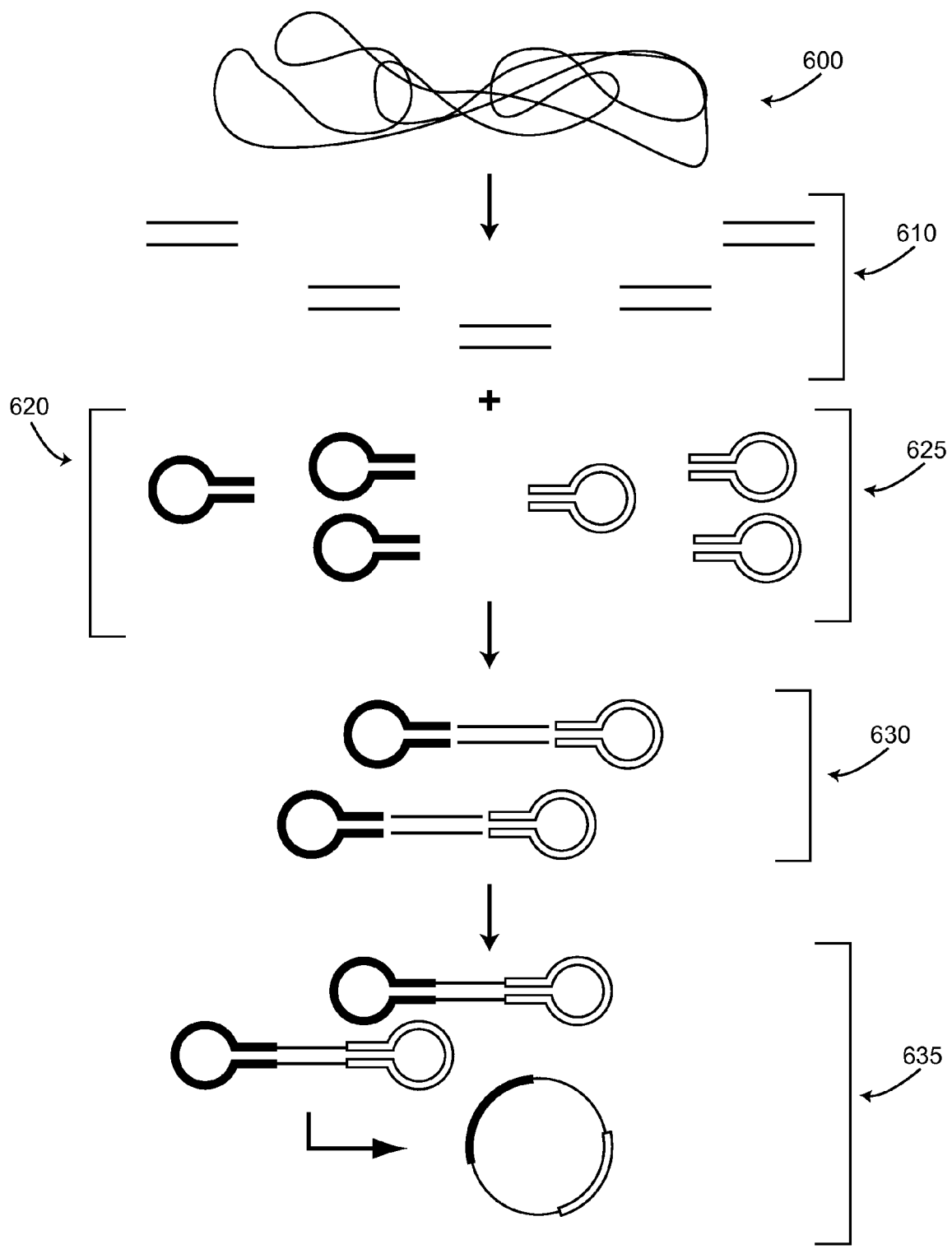
FIG. 6 illustrates methods and compositions for generating single-stranded nucleic acid loops from double-stranded fragments and hairpin oligonucleotides.

The methods include providing double-stranded nucleic acid fragments generated by any one of the strategies described previously. Next, hairpin oligonucleotides are provided to each end of each double-stranded fragment and attached to each end of each fragment, generating a set of single-stranded nucleic acid loops that comprise regions of internal complementarity. These methods are schematically depicted in FIG. 6.

Double-stranded fragments 610 are generated from genomic DNA, cDNA, or a DNA concatamer 600. Procedures for generating double-stranded nucleic acid fragments 610 from genomic DNA, cDNA, or concatamer 600 are described above and are well known in the art. Genomic DNA, cDNA or concatamer 600 can be derived from any of the sources described above.

Next, population of hairpin oligonucleotides 620 is provided to one end of each double-stranded fragment in population 610, and population of hairpin oligonucleotides 625 is provided to the other end of each fragment, as shown in composition 630. The hairpins in population 620 and 625 can be about 20 to about 100 nucleotides in length. In some embodiments, hairpin oligonucleotides 620 and 625 are the same length and, optionally, identical in sequence. In other embodiments, the two populations of hairpins, e.g., 620 and 625, comprise unique sequences, and one population of hairpins can optionally be longer than the other. Either population of hairpins can comprise one or more ligand, fluorescent label, blocking group, phosphorylated nucleotide, phosphorothioated nucleotide, biotinylated nucleotide, methylated nucleotide, nucleotide analog, uracil, a sequence capable of forming a secondary structure, oligonucleotide hybridization site, restriction site, DNA promoter, RNA promoter, sample or library identification sequence, cis regulatory sequence, and/or the like.

In preferred embodiments of the methods, hairpins 620 and 625 anneal to the first and second ends of fragments 610, respectively. For example, hairpins 620 can comprise first single-stranded terminal sequences complementary to second single-stranded terminal sequences at the first ends of fragments 610, and hairpins 625 can comprise third single-stranded terminal sequences complementary to fourth single stranded terminal sequences at the second ends of fragments 610. Attaching hairpins 620 and 625 to fragments 610 can include linking 5' strands of hairpins 620 to 3' strands at the first ends of the fragments 610, linking 3' strands of hairpins 620 to 5' strands at the first ends of fragments 610, linking 5' strands of hairpins 625 to 3' strands at the second ends of fragments 610, and linking 3' strands of hairpins 625 to 5' strands at the second ends of the fragments 610, e.g., via ligation or chemical linkage. Thus, the hairpins are attached to the fragments in a configuration that produces population 635, which comprises closed single-stranded nucleic acid loops with regions of internal complementarity.

Methods of producing closed nucleic acid loops from hairpin for use as templates in rolling circle replication are described in U.S. Pat. No. 6,498,023 B1, by Abarzua, entitled, "Generation of Single-Strand Circular DNA from Linear Self-Annealing Segments." However, the present invention uses self-annealing nucleic acid hairpins with double-stranded nucleic acid fragments, e.g., derived from a genomic DNA, a cDNA, or a DNA concatamer. Because the methods herein produce a heterogeneous population of nucleic acid loops that comprise overlapping sequences of a genomic DNA, cDNA, or DNA concatamer, they can be used as templates provide high-throughput sequencing systems. Accordingly, the heterogeneous templates can be sequenced to generate data that can be assembled to determine the nucleotide sequence of, e.g., a complex mammalian genome.

Composition 630 is provided by the invention. Composition 630 comprises a population of double stranded fragments 610, which comprise overlapping sequences of genomic DNA, cDNA, or DNA concatamer 600. The genomic DNA, cDNA or DNA concatamer 600 can optionally be derived from a eukaryote. Composition 630 includes population of hairpin oligonucleotides 620, and population of hairpin oligonucleotides 625. Hairpin oligonucleotides 620 and/or 625 in composition 630 can optionally comprise or encode any of the additional moieties or sequences described above. Hairpins 620 of the composition 630 can optionally comprise single-stranded terminal sequences that are complementary to second single-stranded terminal sequences at first ends of fragments 610, and hairpins 625 of composition 630 can optionally comprise third single-stranded terminal sequences that are complementary to fourth single-stranded terminal sequences at the second ends of fragments 610. In some embodiments of the compositions, hairpin oligonucleotides 620 and 625 are the same length and, optionally, identical in sequence. In other embodiments, the two populations hairpins, e.g., 620 and 625, comprise unique sequences, and one population of hairpins can optionally be longer than the other. The composition can optionally include a ligase. Further details regarding methods and compositions related to this embodiment can be found in U.S. patent application Ser. No. 12/413,258, filed Mar. 27, 2009.

Methods and Compositions for Generating Single-Stranded Nucleic Acids from Double-Stranded Fragments Using Strand-Displacing Polymerases The following methods and compositions for preparing linear nucleic acid single-stranded nucleic acids, can be used to supply high-throughput sequencing systems with templates in an efficient, timely, and cost-effective manner. Because the methods do not entail cell culture or library construction, they can be scaled to meet the capacity of high-speed next generation sequencing platforms. Advantageously, the methods below produce single-stranded templates, which, unlike double-stranded templates, do not reduce primer annealing efficiency or impede the polymerase-catalyzed extension of a sequencing reaction by reannealing.

In this embodiment, double-stranded fragments are generated from a genomic DNA, a cDNA, or a DNA concatamer, e.g., derived from any one of the sources described previously. Each of the fragments comprises a sacrificial strand and a target strand. The sacrificial strands in each fragment are nicked, e.g., anywhere along the length of the fragment, and displaced from the target strands. Next, sequences on the target strands that are exposed by the displacement of the sacrificial strands are copied by a strand-displacing polymerase to produce linear single-stranded nucleic acids, which can optionally be sequenced, e.g., in a high-throughput sequencing system.

Figure 7:
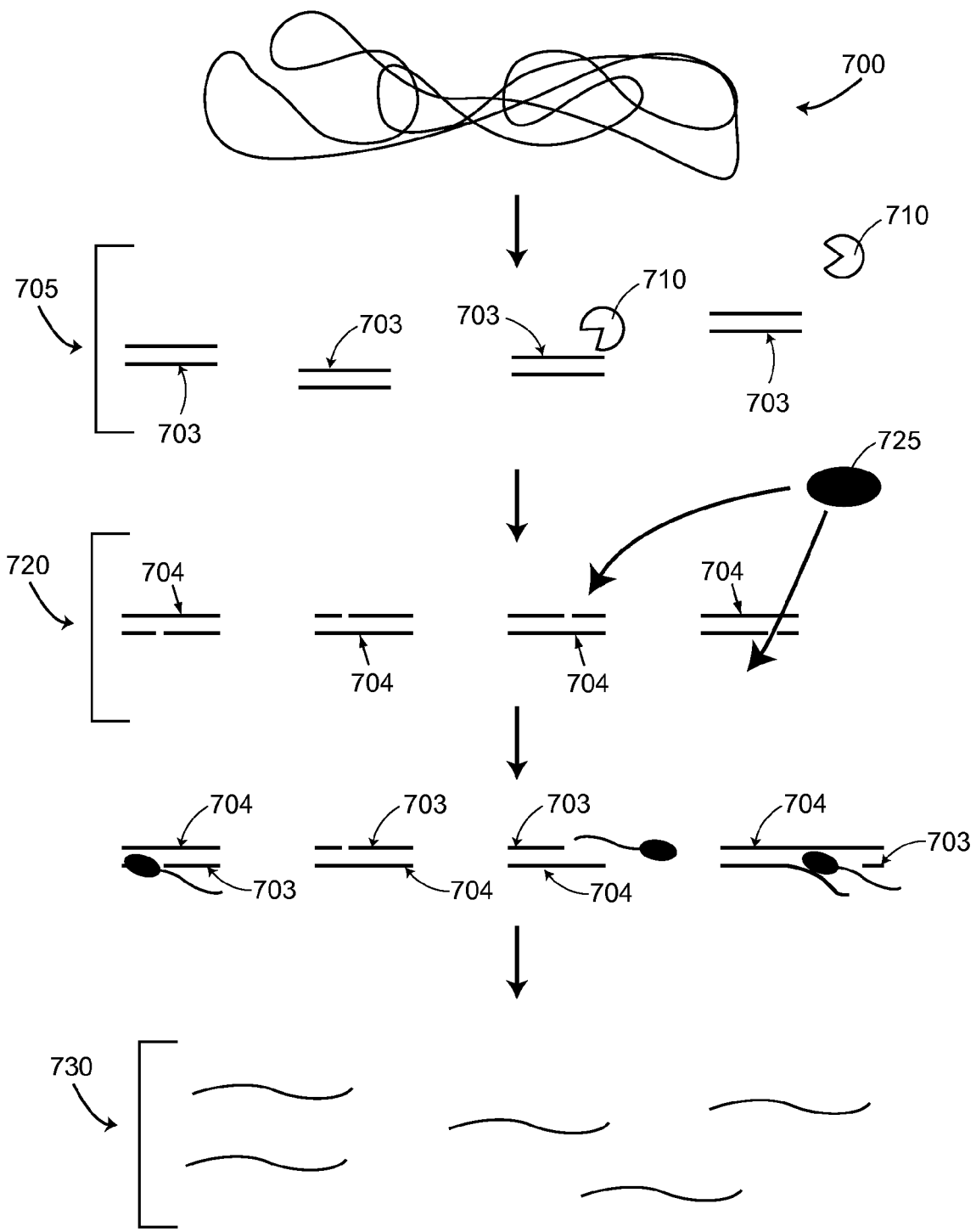
FIG. 7 illustrates methods and compositions for generating linear single-stranded nucleic acids from double-stranded fragments using strand-displacing polymerases.

A schematic of these methods is provided in FIG. 7. Double-stranded fragments 705 can be produced from genomic DNA, cDNA, or DNA concatamer 700 using any of the strategies that have been described above. An advantage to this embodiment is that it does not entail the addition of tags to the fragments. Sacrificial strands 703 of double-stranded fragments 705 are nicked by nicking enzyme 710 to produce population of nicked fragments 720, e.g., double-stranded fragments that comprise one nicked strand. Nicking enzyme 710 can optionally comprise any of the nicking enzymes described previously. Those of skill in the art will appreciate that there exist a myriad of enzymes that can nick a single strand in double-stranded nucleic acid and that those described herein are not to be taken as limiting.

The sacrificial strands of nicked fragments 720 are displaced, e.g., by strand displacing polymerase 725, which then copies the sequences on target strands 704 that are exposed by the displacement of sacrificial strands 703. Strand-displacing polymerases 725 synthesize complementary copies of target strands 704, thereby producing population of single-stranded nucleic acids 730.

Details Regarding Sequencing Reactions and High-Throughput Sequencing Systems.

DNA sequencing refers to methods for determining the order of the nucleotide bases, e.g., adenine, guanine, cytosine, and thymine, in a molecule of DNA, such as a genomic DNA, a cDNA, or a DNA concatamer. Typically, a sequencing reaction mix includes a polymerase; adenine, guanine, cytosine, and thymine nucleotides; a template strand, an oligonucleotide primer that comprises a sequence complementary to a sequence in the template strand, and a divalent cation, e.g., $Mn^{2+}$ or $Mg^{2+}$, which improves the polymerase's activity. In general, a sequencing reaction entails annealing the oligonucleotide primer to the single-stranded DNA template and extending the primer with the polymerase, which incorporates nucleotide bases into a nascent chain to synthesize a DNA molecule whose sequence is complementary to that of the template strand. If a double-stranded template is provided, it is denatured prior to the annealing and extension steps. During synthesis, the incorporation of each individual nucleotide is detected, permitting the determination of the pattern of adenines, guanines, cytosines, and thymines in the template strand.

One sequencing method that is routinely used is chain termination sequencing, in which modified nucleotides that terminate DNA strand elongation. In chain termination sequencing, a sequencing reaction is divided into four separate sequencing reactions, each containing all four of the standard deoxynucleotides, a radiolabeled nucleotide, a template strand, a divalent cation, and a DNA polymerase. To each of the four reactions, one of four dideoxynucleotides (ddATP, ddGTP, ddCTP, or ddTTP) are added. Dideoxynucleotides are chain-terminating nucleotides because they lack a 3'-OH group required for the formation of a phosphodiester bond between two nucleotides, thus terminating DNA strand extension and resulting in various DNA fragments of varying length.

The newly synthesized and labeled DNA fragments are heat denatured, and separated by size (with a resolution of just one nucleotide) by gel electrophoresis on a denaturing polyacrylamide-urea gel with each of the four reactions run in one of four individual lanes (lanes A, T, G, C); the DNA bands are then visualized by autoradiography or UV light, and the DNA sequence can be directly read off the X-ray film or gel image.

Dye-terminator sequencing is a variation of the chain termination methods in which each of the four chain terminator ddNTPs is labeled with a fluorescent dye that has a unique wavelengths of fluorescence and emission. This strategy circumvents the need for four separate reactions, since all four fluorescent signals can be run and read, e.g., in the same lane on a gel or in the same capillary in a capillary electrophoresis system.

The high demand for large-scale sequencing has driven the development of high-throughput sequencing technologies that parallelize the sequencing process, producing thousands or millions of sequences at once. High-throughput sequencing technologies can lower the cost of DNA sequencing beyond what is possible with standard dye-terminator or chain termination methods. Certain commercial high-throughput sequencing systems, e.g., those available from 454 Life Sciences, Illumina, and Pacific Biosciences, are based on multiplexed direct sequencing methods, e.g., "sequencing by synthesis" (SBS), in which each base position in a single-stranded DNA template is determined individually during the synthesis of a complementary strand.

For example, pyrosequencing is a bioluminometric DNA sequencing technique in which the real-time release of the inorganic pyrophosphate (PPi) that is produced upon each successful incorporation of a nucleotide into a DNA is monitored (Nyren (2007) "The History of Pyrosequencing." *Methods Mol Biol* 373: 1-14; Ronaghi (2001) "Pyrosequencing sheds light on DNA sequencing." *Genome Res* 11: 3-11; and Wheeler, et al. (2008) "The complete genome of an individual by massively parallel DNA sequencing." Nature 452: 872-876). In pyrosequencing, PPi release begins an enzymatic cascade in which PPI is immediately converted to ATP by ATP sulfurylase. The ATP then fuels the luciferase-catalyzed oxidation luciferin, in which photons are emitted.

454 Sequencing, a technology available from 454 Life Sciences, is a massively-parallellized, multiplex pyrosequencing system that relies on fixing nebulized, adapter-ligated single-stranded DNA fragments, e.g., which can be prepared by the methods described above, to small DNA-capture beads. The single-stranded DNAs fixed to these beads are then amplified, e.g., via PCR. Each DNA-bound bead is placed into a well on a proprietary PicoTiterPlate™, to which a mix of enzymes, including, e.g., DNA polymerase, ATP sulfurylase, and luciferase, has also been added. The PicoTiterPlate™ is then placed into a sequencing module, where dideoxyribonucleotides, e.g., A, C, G, and T, are washed in series over the PicoTiterPlate™. During the nucleotide flow, the copies of DNA that are attached to the beads are sequenced in parallel. If a nucleotide complementary to a template strand is flowed into a well of the PicoTiterPlate™, the polymerase extends the existing DNA strand by adding the nucleotide, releasing PPi and generating a light signal. The presence or absence of PPi, and, therefore, the incorporation or non-incorporation of each nucleotide washed over the PicoTiterPlate™, is ultimately assessed on the basis of whether or not photons are detected. There is a minimal time lapse between these events, and the conditions of the reaction are such that iterative addition of nucleotides and PPi detection are possible.

Recently, 454 Sequencing technology was used to determine the complete sequence of an individual's genome at a cost of approximately $2,000,000 (Wheeler, et al. (2008) "The complete genome of an individual by massively parallel DNA sequencing." Nature 452: 872-876), a 5-fold reduction in costs compared to that of sequencing an individual's genome using Sanger dideoxy sequencing methods (Levy, et al., (2007) "The Diploid Genome Sequence of an Individual Human." *PLoS Biol* 5: e254).

Currently, single-stranded DNAs are prepared for sequencing in the 454 system by nebulizing genomic DNA and performing Solid Phase Reversible Immobilization (SPRI) step to remove DNA fragments less than 300 base-pairs long prior to attaching the DNA fragments to capture beads (Wheeler, et al. (2008) "The complete genome of an individual by massively parallel DNA sequencing." Nature 452: 872-876, Supplementary Information). However, SPRI removes approximately 10% of the total DNA fragments. In contrast, the methods provided herein avoid the arbitrary loss of genomic sequences inherent in SPRI.

Single-stranded nucleic acid fragments, e.g., prepared using methods described above, can be sequenced using systems that include bridge amplification technologies, e.g., in which primers bound to a solid phase are used in the extension and amplification of solution phase target nucleic acid acids prior to SBS. (See, e.g., Mercier, et al. (2005) "Solid Phase DNA Amplification: A Brownian Dynamics Study of Crowding Effects." *Biophysical Journal* 89: 32-42; Bing, et al. (1996) "Bridge Amplification: A Solid Phase PCR System for the Amplification and Detection of Allelic Differences in Single Copy Genes." Proceedings of the Seventh International Symposium on Human Identification, Promega Corporation Madison, Wis.) Solexa sequencing, available from Illumina, is one such sequencing system.

Single-stranded nucleic acid fragments can be prepared for bridge amplification the following manner: First, unique adapter tags are attached to ends of single-stranded linear nucleic acids during sample preparation. Methods by which the tags are attached to the nucleic acids are not particularly limiting and can include the strategies used to produce tagged double-stranded nucleic acid fragments in the methods detailed above. The nucleic acids to which the adapters have been attached can then be amplified in a "bridged" amplification reaction on the surface of a flow cell. The flow cell surface is coated with single stranded oligonucleotides that correspond to the sequences of the adapters ligated to the linear single-stranded nucleic acids during sample preparation. The single-stranded, adapter-ligated nucleic acids are bound to the surface of the flow cell and exposed to reagents for polymerase-based extension. Priming occurs as the free/distal end of a ligated fragment "bridges" to a complementary oligonucleotide on the surface, and during the annealing step, the extension product from one bound primer forms a second bridge strand to the other bound primer. Repeated denaturation and extension results in localized amplification of single molecules in millions of unique locations, creating clonal "clusters" across the flow cell surface.

The flow cell is then placed in a fluidics cassette within a sequencing module, where primers, DNA polymerase, and fluorescently-labeled, reversibly terminated nucleotides, e.g., A, C, G, and T, are added to permit the incorporation of a single nucleotide into each clonal DNA in each cluster. Each incorporation step is followed by the high-resolution imaging of the entire flow cell to identify the nucleotides that were incorporated at each cluster location on the flow cell. After the imaging step, a chemical step is performed to deblock the 3' ends of the incorporated nucleotides to permit the subsequent incorporation of another nucleotide. Iterative cycles are performed to generate a series of images each representing a single base extension at a specific cluster. This system typically produces sequence reads of up to 20-50 nucleotides. Further details regarding this sequencing system are discussed in, e.g., Bennett, et al. (2005) "Toward the 1,000 dollars human genome." *Pharmacogenomics* 6: 373-382; Bennett, S. (2004) "Solexa Ltd." *Pharmacogenomics* 5: 433-438; and Bentley, D. R. (2006) "Whole genome re-sequencing." *Curr Opin Genet Dev* 16: 545-52.

Single molecule real-time sequencing (SMRT) is another massively parallel sequencing technology that can be used to sequence single-stranded nucleic acid fragments or loops, e.g., produced by any of the methods described herein, in a high-throughput manner. Developed and commercialized by Pacific Biosciences, SMRT technology relies on arrays of multiplexed zero-mode waveguides (ZMWs) in which, e.g., thousands of sequencing reactions can take place simultaneously. The ZMW is a structure that creates an illuminated observation volume that is small enough to observe, e.g., the template-dependent synthesis of a single single-stranded DNA molecule by a single DNA polymerase (See, e.g., Levene, et al. (2003) "Zero Mode Waveguides for Single Molecule Analysis at High Concentrations," *Science* 299: 682-686). When a DNA polymerase incorporates complementary, fluorescently labeled nucleotides into the DNA strand that is being synthesized, the enzyme holds each nucleotide within the detection volume for tens of milliseconds, e.g., orders of magnitude longer than the amount of time it takes an unincorporated nucleotide to diffuse in and out of the detection volume. During this time, the fluorophore emits fluorescent light whose color corresponds to the nucleotide base's identity. Then, as part of the nucleotide incorporation cycle, the polymerase cleaves the bond that previously held the fluorophore in place and the dye diffuses out of the detection volume. Following incorporation, the signal immediately returns to baseline and the process repeats. Additional descriptions of ZMWs and their application in single molecule analyses, such as SMRT sequencing can be found in, e.g., Published U.S. Patent Application No. 2003/0044781, and U.S. Pat. No. 6,917,726, each of which is incorporated herein by reference in its entirety for all purposes. See also, Levene et al. (2003) "Zero Mode Waveguides for single Molecule Analysis at High Concentrations," *Science* 299:682-686 and Eid, et al. (2009) "Real-Time DNA Sequencing from Single Polymerase Molecules." *Science* 323:133-138.

Further Details Regarding Broadly Used Molecular Biology Techniques

Preparing Genomic DNA

Determining the nucleotide sequence of an organism's genome can be useful in a myriad of applications, including, e.g., guiding biological and medical research, identifying an organism's susceptibility to disease, predicting an organism's ecological niche, providing a rational basis for personalized medicine, and others. Because reference genome sequences for many organisms are now publicly available, cataloging sequence variations and understanding their biological consequences has become a major research goal. The invention provides novel methods of producing single-stranded nucleic acids, e.g., linear nucleic acids or nucleic acid loops, from a genomic DNA that can be used to provide templates to a sequencing reaction, e.g., in a high-throughput sequencing system.

Genomic DNA can be prepared from any source, e.g., eukaryotic, prokaryotic, archaeal, viral, etc., by three steps: cell lysis, deproteinization and recovery of DNA. These steps are adapted to the demands of the application, the requested yield, purity and molecular weight of the DNA, and the amount and history of the source. Further details regarding the isolation of genomic DNA can be found in Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2008 ("Sambrook"); Current *Protocols in Molecular Biology*, F. M. Ausubel et al., eds., Current Protocols, a joint venture between Greene Publishing Associates, Inc. and John Wiley & Sons, Inc ("Ausubel"); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley). In addition, many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen.

Preparing cDNA

Alternative splicing (AS) is a major source of protein diversity in higher eukaryotic organisms, and this process is frequently regulated in a developmental stage-specific or tissue-specific manner. Thus, an understanding of changes in splicing patterns can be critical to a comprehensive understanding of biological regulation and disease. Data obtained from sequencing cDNAs can be useful in identifying novel splice variants of a gene of interest and/or in comparing the differential expression of splice isoforms of a gene of interest, e.g., between different tissue types, between different treatments to the same tissue type or between different developmental stages of the same tissue type. The methods for preparing single-stranded nucleic acids, e.g., linear nucleic acids or nucleic acid loops, that are provided by the invention can be beneficially used to produce templates derived from cDNAs to high throughput sequencing systems.

cDNAs are prepared from mRNA. mRNA can typically be isolated from almost any source using protocols and methods described in, e.g., Sambrook and Ausubel. The yield and quality of the isolated mRNA can depend on, e.g., how a tissue is stored prior to RNA extraction, the means by which the tissue is disrupted during RNA extraction, or on the type of tissue from which the RNA is extracted. RNA isolation protocols can be optimized accordingly. Many mRNA isolation kits are commercially available, e.g., the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), and the Easy-mRNA Kit (BioChain). In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountainview, Calif.).

Once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in *cDNA Library Protocols*, I. G. Cowell, et al., eds., Humana Press, New Jersey, 1997, Sambrook and Ausubel. In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services.

Preparing DNA Concatamers

Short sequence tags can be linked together to from long serial molecules termed "concatamers" that can be prepared, e.g., using the methods described herein, for sequencing, e.g., using a high-throughput sequencing system, e.g., a ZMW. A short sequence tag, e.g., 10-14 bp, can contain sufficient information to uniquely identify a transcript, provided that that the tag is obtained from a unique sequence within the transcript. Quantitation of the number of times a particular tag is observed provides the expression level of the corresponding transcript. Thus, sequencing the nucleic acid templates, e.g. prepared according to the methods provided by the invention, derived from concatenated short ESTs, e.g., using a high-throughput sequencing system, can be useful in analyzing global gene expression patterns of, e.g., a tissue at different developmental stages, tissues in different organs from a common genotype, common tissues of different genotypes, common tissues that have been exposed to different treatments, and the like. In addition, sequencing templates, e.g., produced using method described herein, derived from concatamers of short ESTs can eliminate the need for a practitioner to carry out laborious and time-consuming in vivo cloning and cell culturing techniques that are common for other EST-based systems for the analysis of global gene expression, e.g. SAGE (Velculescu, et al. (1995) "Serial analysis of gene expression." *Science* 270: 484-487) and TALEST (Spinella, et al (1999) "Tandem arrays ligation of expressed sequence tags (TALEST): a new method for generating global gene expression profiles." *Nucl Acid Res* 27: e22).

Preparing concatenated ESTs can comprise preparing a cDNA library, e.g., as described above. Typically, the prepared cDNA can then be digested with a restriction enzyme that would be expected to cleave most transcripts at least once, e.g., a restriction enzyme with a 4-base pair recognition site. The 3'-most cDNA fragments are then captured and ligated to adapter molecules that each contain a type-II restriction site, e.g., BsgI, and a second restriction site. Digestion of the adapter-ligated cDNAs, e.g., with BsgI, produces DNA fragments that consist of the adapter itself and an additional 10-12 nucleotides of unknown cDNA sequence separated from the adapter by the restriction site originally used to digest the cDNA. The fragments can then be ligated to a second adapter containing a second restriction site at one end and degenerate overhangs, e.g., which render the second adapter compatible with all possible cDNA sequences, e.g., produced by the BsgI digestion, at the other. The resulting double-tagged DNA molecules can be digested with enzymes that recognize the restriction sites on the adapters and ligated together to form concatamers that can then be prepared, e.g., using the methods described herein, for sequencing, e.g., using a high-throughput system. Additional information and methods describing the preparation of concatamers comprising short ESTs can be found in, e.g., Velculescu, et al. (1995) "Serial analysis of gene expression." *Science* 270: 484-487; Spinella, et al (1999) "Tandem arrays ligation of expressed sequence tags (TALEST): a new method for generating global gene expression profiles." *Nucl Acid Res* 27: e22; WIPO Patent Application Number WO/2004/024953; and Unneberg, et al. (2003) "Transcript identification by analysis of short sequence tags—influence of tag length, restriction site, and transcript database." *Nucl Acids Res* 31: 2217-2226.

Generating Nucleic Acid Fragments

The methods of preparing single-stranded nucleic acids that are described herein entail generating double-stranded fragments from, e.g., a genomic DNA, a cDNA, or a DNA concatamer. There exist a plethora of ways of generating nucleic acid fragments from a genomic DNA, a cDNA, or a DNA concatamer. These include, but are not limited to, mechanical methods, such as sonication, mechanical shearing, nebulization, hydroshearing, and the like; enzymatic methods, such as exonuclease digestion, restriction endonuclease digestion, and the like; and electrochemical cleavage. These methods are further explicated in Sambrook and Ausubel.

Copying Nucleic Acids

In certain embodiments of the methods described herein, populations of double-stranded nucleic acid fragments are produced by copying subsequences, e.g. overlapping subsequences, of a genomic DNA, a cDNA, or a DNA concatamer. A variety of nucleic acid amplification and/or copying methods are known in the art and can be implemented to perform these steps.

The most widely used in vitro technique among these methods is polymerase chain reaction (PCR), which requires the addition of a template of interest, e.g., a DNA comprising the sequence that is to be amplified, nucleotides, oligonucleotide primers, buffer, and an appropriate polymerase to an amplification reaction mix. In PCR, the primers anneal to complementary sequences on denatured template DNA and are extended with a thermostable DNA polymerase to copy the sequence of interest. As a result, a nucleic acid that comprises a sequence complementary to that of the template strand (or "target strand") is synthesized. Repeated cycles of PCR can generate myriad copies. Primers ideally comprise sequences that are complementary to the template. However, they can also comprise sequences that are not complementary, but which comprise e.g., restriction sites, cis regulatory sites, oligonucleotide hybridization sites, protein binding sites, DNA promoters, RNA promoters, sample or library identification sequences, and the like. Primers can comprise modified nucleotides, such as methylated, biotinylated, or fluorinated nucleotides; and nucleotide analogs, such as dye-labeled nucleotides, non-hydrolysable nucleotides, and nucleotides comprising heavy atoms. Primers can be custom synthesized by commercial suppliers as described below. PCR can be a useful means by which to attach tags to fragments. Further details regarding PCR and its uses are described in *PCR Protocols A Guide to Methods and Applications* (Innis et al. eds) Academic Press Inc. San Diego, Calif. (1990) (Innis); Chen et al. (ed) *PCR Cloning Protocols, Second Edition* (Methods in Molecular Biology, volume 192) Humana Press; and in Viljoen et al. (2005) *Molecular Diagnostic PCR Handbook Springer*, ISBN 1402034032.

Additional methods that can be used to amplify, or copy, nucleic acids include strand displacement amplification (SDA), multiple-displacement amplification (MDA), rolling circle replication (RCR). Some methods use RCR to copy single-stranded nucleic acids, e.g., which will be used as templates in sequencing reactions, from double-stranded templates. In RCR, DNA replication is initiated by an initiator protein, e.g., cis A, which nicks one strand of the double-stranded, closed DNA loop at a specific nucleotide sequence called the double-strand origin, or DSO. The initiator protein remains bound to the 5' phosphate end of the nicked strand, and the free 3' hydroxyl end is released to serve as a primer for DNA synthesis by DNA polymerase III. Using the un-nicked strand as a template, replication proceeds around the DNA loop, displacing the nicked strand as single-stranded DNA. Displacement of the nicked strand is carried out by a replisome, e.g., a multiprotein complex that comprises a single-stranded DNA binding protein (SSB), a helicase, a polymerase, and an RCR initiation protein, e.g., cisA.

Further details regarding Rolling Circle Amplification can be found in Demidov, et al, (2002) "Rolling-circle amplification in DNA diagnostics: the power of simplicity," *Expert Rev Mol Diagn* 2: 89-94; Demidov and Broude (eds) (2005) *DNA Amplification: Current Technologies and Applications*. Horizon Bioscience, Wymondham, UK; and Bakht et al. (2005) "Ligation-mediated rolling-circle amplification-based approaches to single nucleotide polymorphism detection" *Expert Rev Mol Diagn* 5: 111-116; Koonin, et al. (1993) "Computer-assisted dissection of rolling circle DNA replication." *BioSystems* 30: 241-268; and Novick (1998) "Contrasting Lifestyles of rolling-circle phages and plasmids." TIBS 23: 434-438.

Copying steps in the methods can be performed with a strand-displacing polymerase. The term "strand displacement" describes the ability of a polymerase to displace downstream DNA encountered during synthesis. Examples of strand-displacing polymerases that can be used with the methods include, e.g., a Phi29 polymerase, a PolI polymerase, a BstI polymerase, or a Phi29-like polymerases, such as those described in U.S. patent application Ser. No. 11/645,223, entitled POLYMERASES FOR NUCLEOTIDE ANALOGUE INCORPORATION.

Nucleic Acid Tags

In some methods of nucleic acid template preparation provided by this invention, tags, e.g., tags comprising phosphorylated 5' ends, can be added to ends of nucleic acid fragments in order to protect the fragments from, e.g., degradation by an exonuclease. In certain other methods, tags comprising specific sequences can be added to the ends of fragments so that the fragments can be, e.g., recognized and nicked by, an e.g., an RCR protein. In other methods, tags comprising, e.g., complementary single stranded terminal sequences, can be added to the ends of fragments to, e.g., promote more efficient circularization of the fragments. The addition of tags, e.g., via ligation, chemical linkage, primer extension, etc. to the ends of nucleic acid fragments is a useful step in the methods for producing single-stranded nucleic acids that are provided by the invention.

Nucleic acid tags can comprise any of a plethora of ligands, such as high-affinity DNA-binding proteins; modified nucleotides, such as methylated, biotinylated, or fluorinated nucleotides; and nucleotide analogs, such as dye-labeled nucleotides, non-hydrolysable nucleotides, or nucleotides comprising heavy atoms. Such reagents are widely available from a variety of vendors, including Perkin Elmer, Jena Bioscience and Sigma-Aldrich. Nucleic acid tags can also include oligonucleotides that comprise specific sequences, such as restriction sites, cis regulatory sites, oligonucleotide hybridization sites, protein binding sites, and the like. Such oligonucleotide tags can be custom synthesized by commercial suppliers such as Operon (Huntsville, Ala.), IDT (Coralville, Iowa) and Bioneer (Alameda, Calif.). The methods that can be used to join tags to nucleic acids of interest include chemical linkage, ligation, and extension of a primer by a polymerase (described above). Further details regarding nucleic acid tags and the methods by which they are attached to nucleic acids of interest are elaborated in Sambrook and Ausubel.

Kits and Articles of Manufacture

Kits are also a feature of the invention. The present invention provides kits that incorporate the compositions of the invention, optionally with additional useful reagents such as one or more enzymes that are used in the methods, e.g., an nicking enzyme polymerase, a DNA polymerase, an RCR protein, etc., that can be unpackaged in a fashion to enable their use. Depending upon the desired application, the kits of the invention optionally include additional reagents, such as a control nucleic acids, buffer solutions and/or salt solutions, including, e.g., divalent metal ions, i.e., $Mg^{2+}$, $Mn^{2+}$, $Ca^{2+}$ and/or $Fe^{++}$, to prepare the single-stranded nucleic acids produced by the methods for sequencing, e.g., in a high-throughput sequencing system. Such kits also typically include a container to hold the kit components, instructions for use of the compositions, and other reagents in accordance with the desired application methods.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of producing a population of closed single-stranded nucleic acid loops, the method comprising:
providing a genomic DNA, a cDNA, or a DNA concatamer;
generating double-stranded nucleic acid fragments from the genomic DNA, the cDNA, or the DNA concatamer, wherein each of said fragments comprises a strand that comprises a gap site;

circularizing the double-stranded nucleic acid fragments, thereby producing nucleic acid loops, wherein each of the nucleic acid loops comprises a non-contiguous strand and a contiguous strand; and removing said non-contiguous strand from each of said nucleic acid loops by digesting said non-contiguous strand with an exonuclease, thereby producing said population of closed single-stranded nucleic acid loops.

2. The method of claim 1, farther comprising using the contiguous strand as a template strand in a sequencing reaction.

3. The method of claim 1, further comprising performing a single-molecule sequencing reaction on said population of closed single-stranded nucleic acid loops.

4. The method of claim 1, wherein said generating the double-stranded nucleic acid fragments comprises:
annealing a population of primer pairs to the genomic DNA, the cDNA, or the DNA concatamer, wherein the primers of said primer pairs comprise the gap site; and
extending the primers annealed with the genomic DNA, the cDNA, or the DNA concatamer with a polymerase, thereby generating the double-stranded nucleic acid fragments.

5. The method of claim 4, wherein the primer pairs comprise one or more moieties selected from: a ligand, a fluorescent label, a blocking group, a phosphorylated nucleotide, a phosphorothioated nucleotide, a biotinylated nucleotide, a methylated nucleotide, a nucleotide analog, a uracil, a sequence capable of forming a secondary structure, an oligonucleotide hybridization site, a restriction site, a DNA promoter, an RNA promoter, a sample or library identification sequence, and a cis regulatory sequence.

6. The method of claim 1, wherein the gap site comprises an unphosphorylated 5' end.

7. The method of claim 1, wherein the gap site comprises a sequence recognized by a nicking enzyme.

8. The method of claim 7, wherein the nicking enzyme is uracil-DNA glycosylase (UNG), uracil-DNA glycosylase (UDG) or a site-specific restriction endonuclease that has been engineered to cleave the gap site.

9. The method of claim 1, wherein the gap site comprises an unphosphorylated 5' end and wherein said producing nucleic acid loops comprises ligating first ends of the double-stranded nucleic acid fragments to second ends of the double-stranded nucleic acid fragments.

10. A method of producing a population of closed single-stranded nucleic acid loops, the method comprising:
providing a genomic DNA, a cDNA, or a DNA concatamer;
cleaving the genomic DNA, the cDNA or the DNA concatamer, thereby producing linear double-stranded nucleic acids;
ligating tags comprising a gap site to the ends of the linear double-stranded nucleic acids, thereby producing double-stranded fragments comprising the gap site;
circularizing the double-stranded nucleic acid fragments, thereby producing a population of nucleic acid loops, wherein each of said population of nucleic acid loops comprises a non-contiguous strand and a contiguous strand; and
removing said non-contiguous strand from each of said population of nucleic acid loops by digesting said non-contiguous strand with an exonuclease, thereby producing said population of closed single-stranded nucleic acid loops.

11. The method of claim 10, wherein said cleaving the genomic DNA, the cDNA, or the DNA concatamer comprises: enzymatic digestion, sonication, mechanical shearing, electrochemical cleavage, or nebulization of the genomic DNA, the cDNA, or the concatamer to produce the linear double-stranded nucleic acids.

12. The method of claim 10, wherein the tags comprise one or more moieties selected from: a ligand, a fluorescent label, a blocking group, a phosphorylated nucleotide, a phosphorothioated nucleotide, a biotinylated nucleotide, a methylated nucleotide, a nucleotide analog, a uracil, a sequence capable of forming a secondary structure, an oligonucleotide hybridization site, a restriction site, a DNA promoter, an RNA promoter, a sample or library identification sequence, and a cis regulatory sequence.

13. The method of claim 10, further comprising performing a single-molecule sequencing reaction on said population of closed single-stranded nucleic acid loops.

14. A method of producing a population of closed single-stranded nucleic acid loops, the method comprising:
providing a genomic DNA, a cDNA or a DNA concatamer;
generating a double-stranded nucleic acid fragments from the DNA, the cDNA or the DNA concatamer, wherein said double-stranded nucleic acid fragments comprise a strand that comprises a gap site, wherein the gap site comprises a sequence recognized by a nicking enzyme;
circularizing the double-stranded nucleic acid fragments by ligating first ends of the double-stranded nucleic acid fragments to second ends of the double-stranded nucleic acid fragments, thereby forming double-stranded nucleic acid loops;
cleaving the strands of the double-stranded nucleic acid loops that comprise the gap site with a nicking enzyme that specifically cleaves the gap site, thereby forming a population of nucleic acid loops, wherein each of said population of nucleic acid loops comprises a non-contiguous strand and a contiguous strand;
removing said non-contiguous strand from each of said population of nucleic acid loops by digesting said non-contiguous strand with an exonuclease, thereby producing said population of closed single-stranded nucleic acid loops.

15. The method of claim 14, further comprising performing a single-molecule sequencing reaction on said population of closed single-stranded nucleic acid loops.

* * * * *